(12) United States Patent
Washington et al.

(10) Patent No.: US 10,912,726 B2
(45) Date of Patent: Feb. 9, 2021

(54) SHAPING KERATIN FIBRES USING A REDUCING COMPOSITION AND A FIXING COMPOSITION

(71) Applicant: The Procter & Gamble Company, Cincinnati, OH (US)

(72) Inventors: Randy Purnell Washington, West Chester, OH (US); David Salloum Salloum, West Chester, OH (US); Curtis Bobby Motley, Hamilton, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 33 days.

(21) Appl. No.: 14/577,100

(22) Filed: Dec. 19, 2014

(65) Prior Publication Data

US 2015/0174023 A1    Jun. 25, 2015

Related U.S. Application Data

(60) Provisional application No. 61/918,154, filed on Dec. 19, 2013.

(51) Int. Cl.
| | |
|---|---|
| *A61K 8/46* | (2006.01) |
| *A45D 7/04* | (2006.01) |
| *A45D 7/06* | (2006.01) |
| *A61K 8/33* | (2006.01) |
| *A61K 8/35* | (2006.01) |
| *A61K 8/362* | (2006.01) |
| *A61K 8/365* | (2006.01) |
| *A61K 8/42* | (2006.01) |
| *A61K 8/49* | (2006.01) |
| *A61K 8/60* | (2006.01) |
| *A61Q 5/04* | (2006.01) |
| *A61Q 5/06* | (2006.01) |
| *A61K 8/34* | (2006.01) |
| *A61K 8/41* | (2006.01) |

(52) U.S. Cl.
CPC ............... *A61K 8/46* (2013.01); *A45D 7/04* (2013.01); *A45D 7/06* (2013.01); *A61K 8/33* (2013.01); *A61K 8/345* (2013.01); *A61K 8/35* (2013.01); *A61K 8/362* (2013.01); *A61K 8/365* (2013.01); *A61K 8/41* (2013.01); *A61K 8/42* (2013.01); *A61K 8/4926* (2013.01); *A61K 8/4973* (2013.01); *A61K 8/60* (2013.01); *A61Q 5/04* (2013.01); *A61Q 5/06* (2013.01); *A61K 2800/30* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,966,903 A | 6/1976 | Torii |
| 4,148,329 A | 4/1979 | Jaskowski |
| 4,364,837 A | 12/1982 | Pader |
| 4,382,765 A | 5/1983 | Moller |
| 4,387,765 A | 6/1983 | Kristoffersson |
| 4,602,143 A | 7/1986 | Mack |
| 4,690,818 A | 9/1987 | Puchalski, Jr. |
| 4,740,669 A | 4/1988 | Takimae |
| 4,795,629 A | 1/1989 | Siuta-Mangano |
| 4,812,307 A | 3/1989 | Siuta-Mangano |
| 4,960,771 A | 10/1990 | Rajadhyaksha |
| 5,110,318 A | 5/1992 | Altobelli |
| 5,578,682 A | 11/1996 | White |
| 5,641,477 A | 6/1997 | Syed |
| 5,858,179 A | 1/1999 | Loda |
| 6,248,979 B1 | 6/2001 | Cafaro |
| 6,255,332 B1 | 7/2001 | Philippe |
| 6,354,305 B1 | 3/2002 | Janouch |
| 6,363,215 B1 | 3/2002 | Cafaro |
| 6,423,942 B1 | 7/2002 | Liao |
| 6,472,478 B1 | 10/2002 | Funk |
| 6,486,105 B1 | 11/2002 | Cannell |

(Continued)

FOREIGN PATENT DOCUMENTS

| | | |
|---|---|---|
| CN | 201504727 U | 6/2010 |
| DE | 19812669 A1 | 10/1999 |

(Continued)

OTHER PUBLICATIONS

Reiger, Martin M. (2000). Harry's Cosmeticology, vols. I-II (8th Edition). Chemical Publishing Company Inc.. Online version available at: http://app.knovel.com/hotlink/toc/id:kpHCVIIIEH/harrys-cosmeticology.*

(Continued)

*Primary Examiner* — Nicole P Babson
(74) *Attorney, Agent, or Firm* — Angela K. Haughey

(57) ABSTRACT

A method for shaping keratin fibres, wherein the method comprises: applying a reducing composition to keratin fibres; rinsing the keratin fibres; applying a fixing composition to keratin fibres, wherein the fixing composition comprises a crosslinking agent, wherein the crosslinking agent has at least two functional groups selected from the group consisting of: —$NH_2$, —NH—, —SH, —OH, —C(=O)H, —C=O, and —COOH, and wherein the crosslinking agent has a molecular weight of 500 g/mol or less; drying the keratin fibres; treating the keratin fibres with a shaping appliance; optionally rinsing the keratin fibres. Also a related use and kit.

2 Claims, 2 Drawing Sheets

(56) References Cited

U.S. PATENT DOCUMENTS

| | | |
|---|---|---|
| 6,488,920 B1 | 12/2002 | Thomas |
| 7,521,926 B2 | 4/2009 | Beck |
| 7,550,136 B2 | 6/2009 | Warner |
| 7,699,058 B1 | 4/2010 | Jay |
| 7,815,900 B1 | 10/2010 | Cannell |
| 8,035,061 B2 | 10/2011 | Jung |
| 8,192,728 B2 | 6/2012 | Paul |
| 8,230,868 B2 | 7/2012 | Choi |
| 8,286,645 B2 | 10/2012 | Kyu |
| 8,349,780 B2 | 1/2013 | Baker |
| 8,424,543 B2 | 4/2013 | Lombardi |
| 8,513,200 B2 | 8/2013 | Dixon |
| 8,883,710 B2 | 11/2014 | Willey |
| 9,414,999 B2 | 8/2016 | Paul |
| 9,415,000 B2 | 8/2016 | Washington |
| 9,713,369 B2 | 7/2017 | Washington |
| 9,781,988 B2 | 10/2017 | Washington |
| 9,872,824 B2 | 1/2018 | Kadir |
| 9,956,155 B2 | 5/2018 | Washington |
| 10,064,799 B2 | 9/2018 | Washington |
| 10,195,130 B2 | 2/2019 | Washington |
| 10,434,051 B2 | 10/2019 | Washington |
| 10,543,156 B2 | 1/2020 | Washington |
| 10,568,826 B2 | 2/2020 | Washington |
| 10,729,630 B2 | 8/2020 | Washington |
| 2001/0013513 A1 | 8/2001 | Chan |
| 2002/0157682 A1 | 10/2002 | Ueyama |
| 2003/0202953 A1 | 10/2003 | Tamareselvy |
| 2004/0000319 A1 | 1/2004 | Carballada |
| 2004/0011373 A1 | 1/2004 | Tsuchiya |
| 2004/0043046 A1 | 3/2004 | Vic |
| 2004/0156800 A1 | 8/2004 | Brun |
| 2004/0206368 A1 | 10/2004 | Warner |
| 2005/0018283 A1 | 1/2005 | Kimura |
| 2005/0048018 A1* | 3/2005 | Fadeeva ............... A61K 8/60 424/70.13 |
| 2005/0058618 A1 | 3/2005 | Evans |
| 2005/0136019 A1 | 6/2005 | Malle |
| 2005/0196369 A1* | 9/2005 | Ueyama ............... A61K 8/35 424/70.2 |
| 2005/0214239 A1 | 9/2005 | Nojiri |
| 2006/0035807 A1 | 2/2006 | Kasturi |
| 2006/0124625 A1* | 6/2006 | Keig ................... A45D 1/04 219/222 |
| 2006/0196523 A1 | 9/2006 | Choi |
| 2006/0257344 A1 | 11/2006 | Nguyen |
| 2007/0028938 A1 | 2/2007 | Tiwari |
| 2007/0106347 A1 | 5/2007 | Lin |
| 2007/0119844 A1 | 5/2007 | Lo |
| 2008/0075682 A1 | 3/2008 | Cassier |
| 2008/0275532 A1 | 11/2008 | Yamazaki |
| 2009/0118421 A1 | 5/2009 | Falk |
| 2009/0126756 A1 | 5/2009 | Syed |
| 2009/0145452 A1 | 6/2009 | Anderson |
| 2009/0155198 A1 | 6/2009 | Vic |
| 2009/0165812 A1 | 7/2009 | Resnick |
| 2009/0283106 A1 | 11/2009 | Torgerson |
| 2009/0285768 A1* | 11/2009 | Baker ................. A61K 8/361 424/59 |
| 2009/0320869 A1 | 12/2009 | Fadeeva |
| 2010/0006116 A1 | 1/2010 | Bell |
| 2010/0037909 A1 | 2/2010 | Gross |
| 2010/0089413 A1 | 4/2010 | Wright |
| 2010/0101598 A1 | 4/2010 | Ng |
| 2010/0132733 A1 | 6/2010 | Kyu |
| 2010/0192970 A1 | 8/2010 | Takahashi |
| 2010/0247800 A1 | 9/2010 | Willey |
| 2010/0269848 A1 | 10/2010 | Morgandi |
| 2010/0300471 A1 | 12/2010 | Malle |
| 2010/0310491 A1* | 12/2010 | Falk ................... A61K 8/06 424/70.122 |
| 2011/0008265 A1 | 1/2011 | Anderson |
| 2011/0017227 A1 | 1/2011 | Samain |
| 2011/0020627 A1 | 1/2011 | Falk |
| 2011/0114108 A1 | 5/2011 | Baker |
| 2011/0253164 A1 | 10/2011 | Morgandi |
| 2011/0256083 A1 | 10/2011 | Smith |
| 2011/0256084 A1 | 10/2011 | Dixon |
| 2012/0192887 A1 | 8/2012 | Vic |
| 2012/0213723 A1 | 8/2012 | Nguyen |
| 2012/0291797 A1 | 11/2012 | Degrood |
| 2012/0312317 A1 | 12/2012 | Mannozzi |
| 2013/0118520 A1 | 5/2013 | Mannozzi |
| 2013/0192625 A1 | 8/2013 | Migliori |
| 2013/0276809 A1 | 10/2013 | Wood |
| 2013/0298933 A1 | 11/2013 | Malle |
| 2013/0299390 A1 | 11/2013 | Koczo |
| 2013/0315852 A1 | 11/2013 | Streuli |
| 2013/0319449 A1 | 12/2013 | Xavier |
| 2013/0340785 A1 | 12/2013 | Baum |
| 2014/0090660 A1 | 4/2014 | Xavier |
| 2014/0190507 A9 | 7/2014 | Xavier |
| 2014/0196741 A1 | 7/2014 | Cabourg |
| 2014/0230842 A1 | 8/2014 | Parris |
| 2014/0235885 A1 | 8/2014 | Koczo |
| 2015/0007876 A1 | 1/2015 | Komai |
| 2015/0020838 A1 | 1/2015 | Kamath |
| 2015/0034119 A1 | 2/2015 | Pressly |
| 2015/0040936 A1 | 2/2015 | Baghdadli |
| 2015/0096584 A1 | 4/2015 | Washington |
| 2015/0128983 A1 | 5/2015 | Vic |
| 2015/0128984 A1 | 5/2015 | Paul |
| 2015/0157561 A1 | 6/2015 | De Graaff |
| 2015/0173478 A1 | 6/2015 | Adams |
| 2015/0173479 A1 | 6/2015 | Adams |
| 2015/0173480 A1 | 6/2015 | Washington |
| 2015/0174027 A1 | 6/2015 | Washington |
| 2015/0174028 A1 | 6/2015 | Washington |
| 2015/0174029 A1 | 6/2015 | Washington |
| 2015/0174030 A1 | 6/2015 | Washington |
| 2015/0174031 A1 | 6/2015 | Washington |
| 2015/0174032 A1 | 6/2015 | Washington |
| 2015/0174035 A1 | 6/2015 | Reed |
| 2015/0174036 A1 | 6/2015 | Washington |
| 2015/0174037 A1 | 6/2015 | Washington |
| 2015/0174432 A1 | 6/2015 | Adams |
| 2015/0174793 A1 | 6/2015 | Adams |
| 2015/0328102 A1 | 11/2015 | Pressly |
| 2015/0374604 A1 | 12/2015 | Kadir |
| 2016/0008243 A1 | 1/2016 | Paul |
| 2016/0158138 A1 | 6/2016 | Baum et al. |
| 2016/0175218 A1 | 6/2016 | Washington |
| 2016/0175219 A1 | 6/2016 | Washington |
| 2016/0175220 A1 | 6/2016 | Washington |
| 2016/0296449 A1 | 10/2016 | Kadir |
| 2016/0317415 A1 | 11/2016 | Washington |
| 2016/0367451 A1 | 12/2016 | Washington |
| 2016/0367459 A1 | 12/2016 | Washington |
| 2017/0035193 A1 | 2/2017 | Vecchiola |
| 2017/0181516 A1 | 6/2017 | Washington |

FOREIGN PATENT DOCUMENTS

| | | |
|---|---|---|
| DE | 102005059936 A1 | 10/2006 |
| EP | 1903034 A1 | 3/2008 |
| EP | 2111852 A2 | 10/2009 |
| FR | 2950247 B1 | 2/2012 |
| FR | 3006585 B1 | 5/2015 |
| GB | 1376136 A | 12/1974 |
| JP | 3629400 B2 | 3/2005 |
| JP | 4950487 B2 | 6/2012 |
| JP | 5086539 B2 | 11/2012 |
| JP | 2013234149 A | 11/2013 |
| KR | 2020060028353 | 9/2007 |
| WO | WO02078655 A2 | 10/2002 |
| WO | WO2004043330 A2 | 5/2004 |
| WO | WO2009045556 A1 | 4/2009 |
| WO | WO2010049623 A2 | 5/2010 |
| WO | WO2010067323 A1 | 6/2010 |
| WO | WO2011074143 A1 | 6/2011 |
| WO | WO2011089985 A1 | 7/2011 |
| WO | WO2012027369 A2 | 3/2012 |
| WO | WO2013092959 A1 | 6/2013 |

(56) References Cited

FOREIGN PATENT DOCUMENTS

| WO | WO2013098332 A2 | 7/2013 |
|---|---|---|
| WO | WO2013117770 A2 | 8/2013 |
| WO | WO2013117843 A1 | 8/2013 |
| WO | WO2013142497 A1 | 9/2013 |
| WO | WO2014001540 A2 | 1/2014 |
| WO | WO2014016658 A1 | 1/2014 |

OTHER PUBLICATIONS

PCT International Search Report and Written Opinion for PCT/US2014/069450 dated Mar. 17, 2015, 14 pages.
Ajinomoto. http://www.ajichem.com/en/products/amino-acids.aspx. Published: Dec. 3, 2008.
All final and non-final office actions for U.S. Appl. No. 14/508,310.
All final and non-final office actions for U.S. Appl. No. 14/576,820.
All final and non-final office actions for U.S. Appl. No. 14/576,866.
All final and non-final office actions for U.S. Appl. No. 14/576,937.
All final and non-final office actions for U.S. Appl. No. 14/576,970.
All final and non-final office actions for U.S. Appl. No. 14/577,003.
All final and non-final office actions for U.S. Appl. No. 14/577,042.
All final and non-final office actions for U.S. Appl. No. 14/577,135.
All final and non-final office actions for U.S. Appl. No. 14/577,186.
All final and non-final office actions for U.S. Appl. No. 14/972,926.
All final and non-final office actions for U.S. Appl. No. 14/972,966.
All final and non-final office actions for U.S. Appl. No. 14/972,993.
All final and non-final office actions for U.S. Appl. No. 15/185,419.
All final and non-final office actions for U.S. Appl. No. 15/185,439.
All final and non-final office actions for U.S. Appl. No. 15/206,595.
All final and non-final office actions for U.S. Appl. No. 15/456,632.
Bobbio. Cienc. Tecnol. Aliment, vol. 20, No. 3, Campas Sep.-Dec. 2003.
Brazil Fabulous. https://web.archieve.org/web/20100402084028/http://brazillianfab.wordpress.com/the-brazilian-keratin-clinic/your-keratin-questions-answered/. Published Apr. 2, 2010.
Brazilian Blowout Zero. http://icanhassscience.com/chemistry/brazilian-blowouts-new-formula-sans-methylene-glycol/. Published Feb. 14, 2011.
Brazilian Keratin. http://www.verticalsinhair.com/index.php?option=com_content&view=category&layout=blow&id=43. Published 2010.
Cut Out + Keep. https://www.cutoutandkeep.net/board/crafts/beauty/4992-how-to-make-bright-hair-dye-stay-in-longer. Published: Aug. 20, 2012.
Edible Medicinal and Non-Medicinal Plants. vol. 3. Lim. Copyright: 2012, pg. 634.
fanci-full. https://web.archive.org/web/2010101803341 1/https://fanci-fullhaircom/fanci/how to use.html. Published: Oct. 18, 2010.
Hinton, A Survey and Critique of the Literature on Crosslinking Agents and Mechanisms as Related to Wool Keratin, School of Textiles, NC State University, 60 pages.
National Center for Biotechnology Information. PubChem Compound Database: CID-1045, https://pubchem.ncbi.nlm.nih.gov/compound/1045 (accessed Aug. 4, 2016).
New World Encyclopedia. "Keratin" http://www.newworldencyclopedia.org/entry/Keratin; available Sep. 19, 2008; accessed May 1, 2016.
PCT International Search Report and Written Opinion for PCT/US2014/058777 dated Jan. 19, 2015.
PCT International Search Report and Written Opinion for PCT/US2014/066627 dated Feb. 18, 2015.
PCT International Search Report and Written Opinion for PCT/US2014/069056 dated Mar. 17, 2015.
PCT International Search Report and Written Opinion for PCT/US2014/069057 dated Mar. 17, 2015.
PCT International Search Report and Written Opinion for PCT/US2014/069059 dated Mar. 19, 2015.
PCT International Search Report and Written Opinion for PCT/US2014/069061 dated Mar. 18, 2015.
PCT International Search Report and Written Opinion for PCT/US2014/069450 dated Mar. 17, 2015.
PCT International Search Report and Written Opinion for PCT/US2014/069451 dated Apr. 21, 2015.
PCT International Search Report and Written Opinion for PCT/US2014/071436 dated Apr. 9, 2015.
PCT International Search Report and Written Opinion for PCT/US2014/071455 dated Apr. 9, 2015.
PCT International Search Report and Written Opinion for PCT/US2015/065670 dated Mar. 31, 2016.
PCT International Search Report and Written Opinion for PCT1US20151065673 dated Mar. 10, 2016.
PCT International Search Report and Written Opinion for PCT/US2015/065674 dated Mar. 14, 2016.
PCT International Search Report and Written Opinion for PCT/US2016/037959 dated Sep. 19, 2016.
PCT International Search Report and Written Opinion for PCT/US2016/037961 dated Sep. 21, 2016.
ThermoScientific https://tools.thermofisher.com/content/sfs/manuals/MAN0011369_BM_PEG2_BM_PEG3_UG.pdf available Feb. 28, 2006; accessed May 1, 2016.
Tuliao Gongye, vol.39, Issue8, pp.15-19, 23, Journal (Chinese) 2009.
Whole World Botanicals, http://wholeworldbotanicals.cornicamu-camu-myrciaria-dubia/. Published Mar. 1, 2003.

* cited by examiner

SHAPING KERATIN FIBRES USING A REDUCING COMPOSITION AND A FIXING COMPOSITION

FIELD OF THE INVENTION

A method for shaping keratin fibres, wherein the method comprises: applying a reducing composition to keratin fibres; rinsing the keratin fibres; applying a fixing composition to keratin fibres, wherein the fixing composition comprises a crosslinking agent, wherein the crosslinking agent has at least two functional groups selected from the group consisting of: $-NH_2$, $-NH-$, $-SH$, $-OH$, $-C(=O)H$, $-C=O$, and $-COOH$, and wherein the crosslinking agent has a molecular weight of 500 g/mol or less; drying the keratin fibres; treating the keratin fibres with a shaping appliance; optionally rinsing the keratin fibres.

BACKGROUND OF THE INVENTION

Styling hair is about achieving a specific hairstyle e.g. achieving straight hair from curly hair, or achieving curly hair from straight hair. Hair may be styled using non-permanent and/or permanent methods. Additionally, consumers use a myriad of chemical treatments with and without external tools such as flat irons, blow dryers, etc to achieve and maintain a certain hairstyle.

Permanent methods—or relaxers—usually comprise the steps of applying onto hair a composition comprising a high pH solution (or combination of components to generate high pH), leaving on for a protracted time and then applying a neutralizing composition. A relaxer is a treatment predominately used by people of African-descent to permanently straighten hair. The treatment relies on either the one-step sodium hydroxide (lye) or a two step (e.g. guanidine carbonate and calcium hydroxide) to achieve very high pH (pH 12-14).

Semi-permanent benefits can be achieved using redox chemistry comprising a reducing agent and an oxidation agent. One such reducing agent commonly employed is thioglycolic acid (TGA), with a subsequent fixation step comprising an oxidation agent such as hydrogen peroxide. Here, the curly hair is transformed into straight hair because the disulfide bonds are broken by the reaction with TGA. The straighter style is locked in during the fixation step with hydrogen peroxide causing reformation of the disulphide bonds into the new configuration.

US20090320869A1 (Fadeeva et al) relates to methods for preventing reversion of at least one relaxed keratinous fiber and for relaxing at least one keratinous fiber comprising applying compositions comprising at least one sugar chosen from $C_3$ to $C_5$ monosaccharides and heating at least one keratinous fiber. US20090320869A1 mentions in example 5 thioglycolate cream and hydrogen peroxide cream. WO2012027369 (Weinmaster et al) relates to systems and methods of straightening or shaping (e.g., curling or waving) hair, comprising: a) applying an aqueous reducing composition to the hair, comprising an effective amount of a consumable reducing agent, a first amino acid, and a first C2-C10 carboxylic acid; b) applying an aqueous fixing composition to the rinsed hair, wherein the fixing composition comprises a second amino acid, a second C2-C10 carboxylic acid, and a hair conditioning agent, wherein the first and second amino acids and the first and second C2-C10 carboxylic acids may be the same or different; and c) straightening or shaping the hair.

The known methods for straightening hair have drawbacks. The permanent methods (relaxers) are typically time-consuming and may damage hair. In addition, such methods show little flexibility so that any need and/or wish for changing the hairstyle would require conducting again a "permanent" wave onto hair, which is time-consuming and further damages the hair.

Along with the potential for skin irritation during application, relaxers tend to permanently change the hair by breaking the natural disulfide bonds in the hair. This leaves the hair weaker and more prone for further breakage. Over-processing can also increase hair damage and skin irritation.

Likewise, semi-permanent methods also have drawbacks. Consumer products using redox chemistry can also have damage if the hair is over-processed during the fixation step—leading to hair breakage and/or discolouration. Therefore, providing a semi-permanent style without the drawbacks traditionally associated with the fixation step is desirable for the overall health and appearance of the hair. There is also a need for providing a method for achieving and semi-permanently retaining and/or recovering a hairstyle using reducing agents with lower hair damage and hair discoloration than those using an oxidising agent in the fixation step. There is also the desire for providing a method for obtaining a hairstyle exhibiting resistance to shampoo treatments. Particularly, there is a need for providing a method for retaining and/or recovering hairstyle after at least one shampoo treatment, particularly after five shampoo treatments, more particularly after ten shampoo treatments. Also, there is a need for providing more economic semi-permanent hair shaping treatments.

SUMMARY OF THE INVENTION

A first aspect of the invention relates to a method for shaping keratin fibres, wherein the method comprises:
  (a) applying a reducing composition to keratin fibres, wherein the reducing composition comprises reducing agent;
  (b) rinsing the keratin fibres and optionally drying the keratin fibres;
  (c) applying a fixing composition to keratin fibres, wherein the fixing composition comprises a crosslinking agent; wherein the crosslinking agent has at least two functional groups selected from the group consisting of: $-NH_2$, $-NH-$, $-SH$, $-OH$, $-C(=O)H$, $-C=O$, and $-COOH$; and wherein the crosslinking agent has a molecular weight of 500 g/mol or less;
  (d) drying the keratin fibres;
  (e) treating the keratin fibres with a shaping appliance;
  (f) optionally rinsing the keratin fibres;
  wherein the method does not use an oxidising agent, preferably does not use peroxide;
  and wherein the keratin fibres are not rinsed between or during steps (c) to (e).

A second aspect of the invention relates to the use of a fixing composition for oxidising cysteine residues into disulphide bonds, wherein the crosslinking agent has at least two functional groups selected from the group consisting of: $-NH_2$, $-NH-$, $-SH$, $-OH$, $-C(=O)H$, $-C=O$, and $-COOH$; and wherein the crosslinking agent has a molecular weight of 500 g/mol or less.

A third aspect of the invention relates to a kit comprising:
  a reducing composition, wherein the reducing composition comprises a reducing agent;
  a fixing composition, wherein the fixing composition comprises a crosslinking agent;

wherein the crosslinking agent has at least two functional groups selected from the group consisting of: —NH$_2$, —NH—, —SH, —OH, —C(=O)H, —C=O, and —COOH; and wherein the crosslinking agent has a molecular weight of 500 g/mol or less.

optionally an appliance for mechanically shaping hair.

DETAILED DESCRIPTION OF THE INVENTION

Definitions and General

Figure 1:
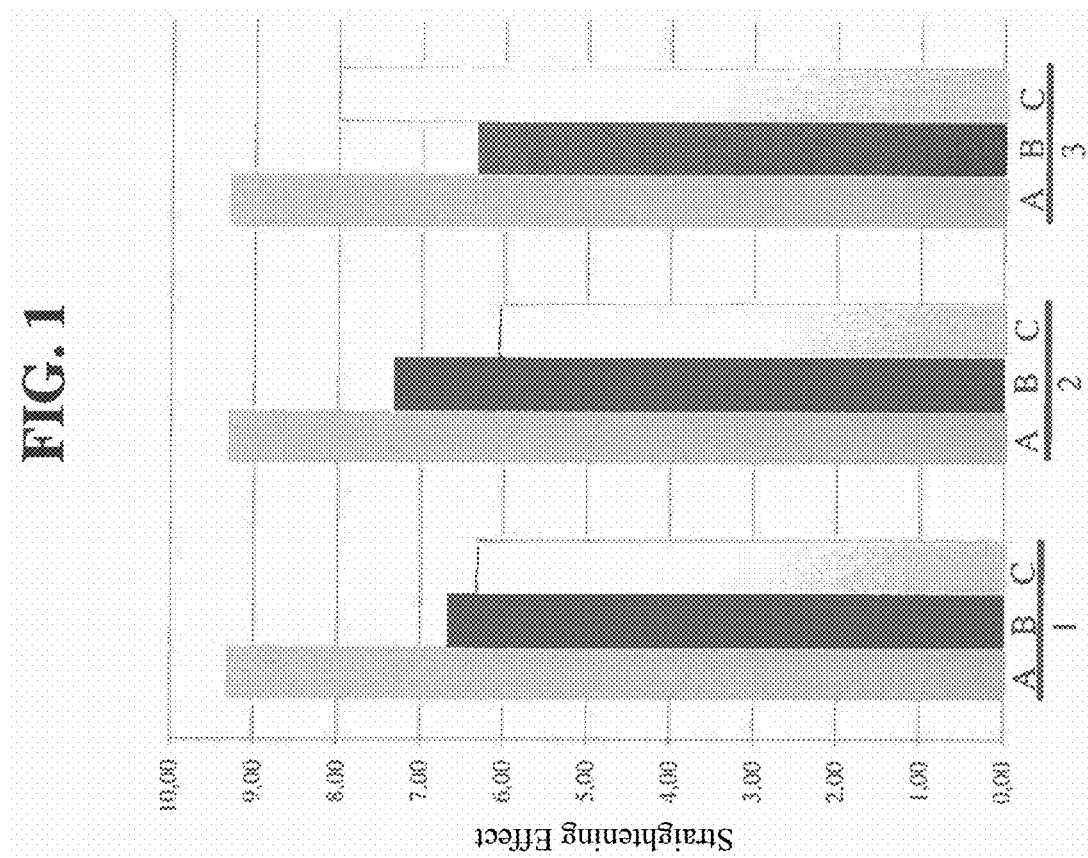
FIG. 1 shows the straightening effect (presented as a bar chart) of hair treated with the method of the present invention versus comparative methods. Durability of the treatment is also tested. 1=10% thioglycolic acid (TGA); 2=10% TGA+H$_2$O$_2$; 3=10% TGA+5% arabinose. In relation to the individual bars: A=immediately after treatment; B=after 1 wash; C=after 10 washes.

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All measurements are understood to be made at 25° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International. Herein: "min" means "minute" or "minutes"; "mol" means mole; "nanometers" is abbreviated "nm"; "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol, would fall within the scope.

"Molecular weight" or "M.Wt." or "MW" and grammatical equivalents thereof mean the number average molecular weight.

"Viscosity" is measured at 25° C. using a HAAKE Rotation Viscometer VT 550 with cooling/heating vessel and sensor systems according to DIN 53019 at a shear rate of 12.9 s$^{-1}$.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than 1%, or less than 0.8%, or less than 0.5%, or less than 0.3%, or about 0%, by total weight of the composition or formulation.

"Dry" or "substantially dry" means comprising less than 5%, less than 3% or, less than 2%, less than 1%, or about 0% of any compound or composition being in liquid form when measured at 25° C. at ambient conditions. Such compounds or compositions being in liquid form include water, oils, organic solvents and other wetting agents. "Anhydrous" means that the composition comprises less than 5%, less than 3% or, less than 2%, less than 1%, or about 0% water by total weight of the composition.

"Keratin fibres" means fibrous material composed of keratin. "Hair" means mammalian keratin fibres including scalp hair, facial hair and body hair. It includes such hair still being attached to a living subject and also hair that has been removed therefrom such as hair swatches and hair on a doll/mannequin. In at least one embodiment, "hair" means human hair. "Hair shaft" or "hair fibre" means an individual hair strand and may be used interchangeably with the term "hair."

"Proximal to the scalp" means that portion of an extended, or substantially straightened, hair shaft that is closer in distance to the scalp than to the end of the hair. Thus, 50% of the hair fibre length would be considered proximal to the scalp, and 50% of the hair fibre would be distal to the scalp. "z cm proximal to the scalp" means a distance "z" along the hair, with one endpoint being on or directly adjacent to the scalp, and the second endpoint being measured "z" centimetres along the length of the extended or substantially straightened hair.

"Chemically modify" or grammatical equivalents thereof, means that a chemical moiety such as monomer and/or crosslinker and/or polymer, stably affixes to a second chemical moiety, for example, a keratin protein, another component of hair, and/or another monomer or crosslinker or polymer. Normally, "chemically modify" means stably affix via a covalent bond, unless otherwise stated.

"Cosmetically acceptable" means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives" includes but is not limited to, amide, ether, ester, amino, carboxyl, acetyl, acid, salt and/or alcohol derivatives of a given compound. In at least one embodiment, "derivatives thereof" means the amide, ether, ester, amino, carboxyl, acetyl, acid, salt and alcohol derivatives.

"Monomer" means a discrete, non-polymerised chemical moiety capable of undergoing polymerisation in the presence of an initiator or any suitable reaction that creates a macromolecule e.g. such as polycondensation, polyaddition, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Kit" means a package comprising a plurality of components. "Kit" may be referred to as "kit-of-parts". An example of a kit is a first composition and a separately packaged second composition and optionally application instructions.

Description of the Invention

The present invention relates inter alia to a hair shaping method e.g. for achieving a semi-permanent hairstyle. The present method comprises treating hair with a reducing composition comprising a reducing agent, followed by rinsing and fixation with a fixing composition comprising an crosslinking agent, drying and shaping steps—creating a semi-permanent hairstyle i.e. a durable hairstyle. This semi-permanent hairstyle is retained after at least one shampoo treatment, particularly after five shampoo treatments, more particularly after 10 shampoo treatments. Besides the increased durability of the hairstyle, this method prevents clumping of hair and/or improves post-shampoo detangling of hair and feel. In addition, the inventors have found that this method increases the water-resistance of hairstyle, increases the ease of style and/or increases the manageability of the hairstyle after shampooing. Without wishing to be bound by theory, it is believed that the above benefits are due to the steps conducted, their sequence, as well as the specific components used including the selected crosslinking agent. Another advantage of the invention is being able to achieve the semi-permanent benefits with natural or naturally-derived crosslinking agents. It is understood that the selected crosslinking agent diffuses into the hair and crosslinks the hair providing sufficient crosslinks to reform the disulphide bonds in the desired configuration. This results in a durable hairstyle.

The details of the different aspects of the invention are described hereinafter. The present invention relates inter alia to a method for shaping keratin fibres. The method comprises applying a reducing composition to keratin fibres.

Reducing Composition

The reducing composition comprises reducing agent. In at least one embodiment, the reducing agent is capable of reducing disulphide bonds in keratin fibres. In at least one embodiment, the reducing agent is selected from the group consisting of: cosmetically acceptable salts, esters (e.g. lower alkyl), amines, sulfites, di sulfite s , bisulfites, metabisulfites, hydrosulfites, hyposulfites, pyrosulfites, mercaptans, phosphines, and mixtures thereof. Both anhydrous and hydrated forms of these agents may be used. In at least one embodiment, the reducing agent is an amine and wherein the amine is selected from the group consisting of: triethanolamine (TEA), monoethanolamine (MEA) and aminomethyl propanol (AMP), and mixtures thereof. In at least one embodiment, the reducing agent is a cosmetically acceptable salt selected from the group consisting of: alkali metal salts (such as sodium salts and potassium salts) and ammonia salts. In at least one embodiment, the reducing agent is selected from the group consisting of: thioglycolic acid, carboxymethyl phosphine, thiolactic acid, 3-mercaptopropionic acid, 2-hydroxy-3-mercaptopropionic acid, cysteine, cysteamine, alkyl- or acylcysteamine with 1 to 4 carbon atoms in the alkyl residue, or the salts thereof; cysteine-(2-hydroxyethyl)ester, L-cysteine glycerine ester, glycerine mono thioglycolate, and mixtures thereof. In at least one embodiment, the reducing agent is selected from the group consisting of: thioglycolate, thiolactate, cysteine, cysteamine, and mixtures thereof. In at least one embodiment, the reducing agent is selected from the group consisting of: thioglycolate, thiolactate, and mixtures thereof. In at least one embodiment, the reducing agent is carboxymethyl phosphine.

In at least one embodiment, the reducing composition comprises reducing agent in an amount effective to reduce (break) disulphide bonds in hair in order to allow the hair to be straightened or shaped. In at least one embodiment, the reducing composition comprises from 0.1% to 20%, or from 1% to 15%, or from 2% to 12%, or from 5% to 11%, or from 8% to 10% reducing agent.

In an embodiment, the reducing composition further comprises a dithioglycolate compound and/or a dithiolactate compound. In an embodiment, the reducing composition further comprises diammonium dithioglycolate and/or diammonium dithiolactate. The dimeric versions of ammonium thiolactate and ammonium thiolactate, namely diammonium dithioglycolate and diammonium dithiolactate, respectively, are useful in that they help regulate the availability of a thioglycolate ion or thiolactate ion to the hair via the formation of an equilibrium. The thioglycolate ion has the chemical formula HS—$CH_2$—$COO^-$ and the thiolactate ion has the chemical formula HS—$CH(CH_3)$—$COO^-$.

In at least one embodiment, the reducing composition comprises a hair swelling and penetration enhancing substance. In at least one embodiment, the hair swelling and penetration enhancing substance is selected from the group consisting of: urea, melamine, ethers, e.g. dipropyleneglycol monomethyl ether; 2-pyrrolidone, imidazolidin-2-one, resorcinol, 1-methyl-2-pyrrolidone, glycerine, propylene glycol, alkali or ammonium thiocyanate, polyvalent alcohols, isopropanol, and mixtures thereof. In at least one embodiment, the reducing composition comprises from 1% to 30%, or from 2% to 15%, or from 5% to 10% hair swelling and penetration enhancing substance. In at least one embodiment, the hair swelling and penetration enhancing substance is urea and the composition comprises from 1% to 30%, or from 10% to 20%, or from 12% to 15% urea.

In at least one embodiment, the reducing composition comprises an alkalising agent. In at least one embodiment, the reducing composition comprises from 0.5% to 1.5% alkalising agent. The alkalising agent is useful in keeping the pH high enough, e.g. above pH 7. In at least one embodiment, the alkalising agent is ammonia. In at least one embodiment, the reducing composition comprises from 0.1% to 3%, or from 0.2% to 1.9%, or from 0.3% to 1.8%, or from 0.4% to 1.7%, or from 0.4% to 1.7%, or from 0.5% to 1.6%, or from 0.6% to 1.5%, or from 0.7% to 1.4%, or from 0.8% to 1.3%, or from 0.9% to 1.2% ammonia. Ammonia is useful as alkalising agent because it is well-known to the stylist and cosmetic formulator. In at least one embodiment, the reducing composition is substantially free of monoethanolamine.

In at least one embodiment, the reducing composition has a pH of from pH 7.5 to pH 11.5. In an embodiment reducing composition has a pH of from pH 8 to pH 10, or from pH 7.5 to pH 9.5, or from pH 7.75 to pH 9.25, or from pH 8.0 to pH 9.0.

In at least one embodiment, the reducing composition comprises from 2.0% to 10% conditioning agent. In at least one embodiment, the conditioning agent is selected from the group consisting of: silicone compounds; cationic surfactants; and mixtures thereof. In at least one embodiment, the reducing composition comprises a mixture of polydimethylsiloxane and terminal aminosilicone. In at least one embodiment, the reducing composition is substantially free of any silicone compound comprising pendant amino groups.

In at least one embodiment, the reducing composition comprises a thickening polymer. In at least one embodiment, the thickening polymer is a polyquaternium compound.

In at least one embodiment, the reducing composition has a viscosity of from 500 mPa·s to 5500 mPa·s, or from 3000 mPa·s to 4500 mPa·s, measured at 25° C. The viscosity in mPa·s is measured with a Haake Rheometer VT-550, Measure system: MV-DIN, Shear rate: 12.9 s$^{-1}$. The viscosity range is useful in view of the avoidance of dripping during use and application onto hair.

The reducing composition may be in the form of a pourable liquid (under ambient conditions). In at least one embodiment, the reducing composition comprises a cosmetically acceptable aqueous carrier and is in the form of a pourable liquid. In at least one embodiment, the reducing composition comprises a cosmetically acceptable aqueous carrier present at a level of from 20% to 95%, or from 60% to 85%. The cosmetically acceptable aqueous carrier may be selected from the group consisting of water and water solutions of lower alkyl alcohols and polyhydric alcohols. The lower alkyl alcohols may be monohydric alcohols having 1 to 6 carbons. In an embodiment, the lower alkyl alcohols are ethanol and isopropanol. The polyhydric alcohols may be propylene glycol, hexylene glycol, glycerin, and propane diol.

Fixing Composition

The hair shaping method of the present invention comprises applying a fixing composition to keratin fibres, wherein the fixing composition comprises a crosslinking agent, wherein the crosslinking agent has at least two functional groups selected from the group consisting of: —NH$_2$, —NH—, —SH, —OH, —C(=O)H, —C=O, and —COOH; and wherein the crosslinking agent has a molecular weight of 500 g/mol or less. In at least one embodiment, the crosslinking agent has a molecular weight of 400 g/mol or less. In at least one embodiment, the crosslinking agent has a molecular weight of 300 g/mol or less, or from 50 g/mol to 250 g/mol, or from 80 g/mol to 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is liquid at 25° C. Crosslinking agents being liquid at this temperature have the advantage of providing improved hair feel versus crosslinking agents that are solid at this temperature.

In at least one embodiment, the crosslinking agent is capable of crosslinking keratin. In at least one embodiment, the crosslinking agent is selected from the group consisting of: diols, carboxylic acids, amines, diamines, reducing sugars, carbonyls, carboxylic acids, and mixtures thereof. In at least one embodiment, the crosslinking agent comprises at least two reactive sites selected from the functional groups consisting of: aldehyde, hydroxyl, carboxyl, and combinations thereof. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, ribose, arabinose, xylose, lyxose, galactose, mannose, 3-(2-hydroxyethyl)-2-oxazolidinone, hexane-2,5-dione, butane-2,3-dione, ethanedial, 2-hydroxy-butanedial, 4-oxo-pentanoic acid, 1,4-butanediol, 1,6-hexanediol, 1,2,4-butanetriol, 1,2,6-hexanetriol, butanedioic acid, heptanedioic acid, oxoethanoic acid, 2,2-dihydroxyethanoic acid, 2,2'-oxybis(2-hydroxy)-ethanoic acid, 2-hydroxypropane-1,2,3-tricarboxylic acid, 1,2,3,4-butanetetracarboxylic acid, 1,3-dioxolan-2-one, dimethyl carbonate, diethyl carbonate, diphenyl carbonate; 1,3-dioxan-2-one, 4-methyl-1,3-dioxolan-2-one, and mixtures thereof. In at least one embodiment, the crosslinking agent is selected from the group consisting of: ribose, arabinose, oxoethanoic acid, 2,2-dihydroxyethanoic acid, 2-hydroxypropane-1,2,3-tricarboxylic acid, 1,2,3,4-butanetetracarboxylic acid, 1,3-dioxolan-2-one, and mixtures thereof.

In at least one embodiment, the fixing composition comprises from 0.1% to 40% crosslinking agent. In at least one embodiment, the composition comprises from 1% to 20%, or from 0.1% to 15%, or from 1% to 12%, or from 2% to 10% crosslinking agent.

In at least one embodiment, the fixing composition comprises a crosslinking agent, wherein the crosslinking agent is an amine or diamine. Amines are useful because they are often naturally-derived (e.g. glycine), which is preferred by consumers versus synthetic compounds. This is not only for perceived health and lack of sensitisation reasons, but also for sustainability and environmental reasons—amines usually break down naturally, quickly and do not require special disposal methods. Also, some amines are liquid at 25° C., which is useful from a feel perspective—consumers, when touching their keratin fibres, feel reduced roughness and friction versus actives being solid at 25° C. In at least one embodiment, the crosslinking agent is liquid at 25° C. The crosslinking agent is an amine or diamine; wherein the crosslinking agent has at least two functional groups selected from the group consisting of: —NH$_2$, —NH—, —SH, —OH, —C(=O)H, —C=O, and —COOH; and wherein the crosslinking agent has a molecular weight of 500 g/mol or less. In at least one embodiment, the crosslinking agent has a molecular weight of 400 g/mol or less, or 300 g/mol or less, or from 50 g/mol to 250 g/mol, or from 80 g/mol to 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle.

In at least one embodiment, the crosslinking agent is a primary or secondary amine. Amines usually include an organic species bearing at least one nitrogen atom as part of a functional group. Amines may be mono-amines bearing one functional group comprising at least one nitrogen atom, diamines bearing two functional groups each comprising at least one nitrogen atom or polyamines bearing more than two functional groups each comprising at least one nitrogen atom. In a primary amine the nitrogen atom bears two hydrogen atoms and one organic moiety. In a secondary amine in which the nitrogen atom bears one hydrogen atoms and two organic moieties. In at least one embodiment, the organic moiety or moieties is/are independently selected from the group consisting of: $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ hydroxy, $C_1$-$C_{32}$ alkoxy, $C_1$-$C_{32}$ substituted alkoxy, $C_1$-$C_{32}$ alkylamino, and $C_1$-$C_{32}$ substituted alkylamino, —OH, —$NH_2$, and =NH.

In at least one embodiment, the crosslinking agent comprises at least one further functional group. In at least one embodiment, the further functional group is any organic moiety comprising at least one of an Oxygen, Nitrogen, Phosphorous, Boron or Sulfur atom. In at least one embodiment, the further functional group is selected from the group consisting of: Hydroxyl, Carbonyl, Aldehyde, Haloformyl, Carbonate ester, Carboxylate, Carboxyl, Ester, Methoxy, Hydroperoxy, Peroxy, Ether, Hemiacetal, Hemiketal, Acetal, Ketal, Orthoester, Orthocarbonate ester, Carboxamide, Primary amine, Secondary amine, Tertiary amine, Ammonium, Primary ketimine, Secondary ketimine, Primary aldimine, Secondary aldimine, Imide, Azide, Azo or Diimide, Cyanate, Isocyanate, Nitrate, Nitrile, Isonitrile, Nitrosooxy, Nitro, Nitroso, Pyridyl, Sulfhydryl, Sulfide, Disulfide, Sulfinyl, Sulfonyl, Sulfino, Sulfo, Thiocyanate, Isothiocyanate, Carbonothioyl, Carbonothioyl, Phosphino, Phosphono, Phosphate, Borono, Boronate, Borino, Borinate. In at least one embodiment, the crosslinking agent is a polyamine.

In at least one embodiment, the crosslinking agent is a diamine. In at least one embodiment, the crosslinking agent is a diamine conforming to the formula $H_2N$—$(CH_2)n$-$NH_2$, wherein n is an integer from 3 to 12, and isomers thereof. In at least one embodiment, the crosslinking agent is a diamine conforming to the formula $H_2N$—$(CH_2)n$-$NH_2$, wherein n is an integer from 2 to 12, or from 4 to 10, or from 5 to 8, and isomers thereof. 2-methylpropane-1,3-diamine is isomer of 1,4-diaminobutane. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, and mixtures thereof. In at least one embodiment, the crosslinking agent is a diamine and wherein the diamine is selected from the group consisting of: 1,2-diaminoethane, 1,3-diaminopropane, 2-methylpropane-1,3-diamine, 1,4-diaminobutane, 1,5-diaminopentane, 1,6-diaminohexane, 1,7-diaminoheptane, 1,8-diaminooctane, 1,9-diaminononane, 1,10-diaminodecane, and mixtures thereof. In at least one embodiment, the crosslinking agent is a diamine and wherein the diamine is selected from the group consisting of: 1,7-diaminoheptane, 1,4-diaminobutane, and mixtures thereof. 1,4-diaminobutane has a molecular weight of 88 g/mol and 1,7-diaminoheptane has a molecular weight of 130 g/mol. In at least one embodiment, the crosslinking agent comprises a thiol group. In at least one embodiment, the crosslinking agent is 2-aminoethanethiol.

In at least one embodiment, the crosslinking agent is a sugar. Sugars are useful because they are naturally-derived, which is preferred by consumers versus synthetic compounds. This is not only for perceived health and lack of sensitisation reasons, but also for sustainability and environmental reasons—sugars break down naturally and quickly and do not require special disposal methods. Furthermore, sugars are also easy to source and relatively inexpensive. The crosslinking agent has a molecular weight of 500 g/mol or less. In at least one embodiment, the crosslinking agent has a molecular weight of 300 g/mol or less, or from 50 g/mol to 250 g/mol, or from 80 g/mol to 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle. In at least one embodiment, the crosslinking agent is liquid at 25° C. Crosslinking agents being liquid at this temperature have the advantage of providing improved hair feel versus crosslinking agents that are solid at this temperature. In at least one embodiment, the crosslinking agent is a monosaccharide. In at least one embodiment, the sugar is a monosaccharide and wherein the fixing composition comprises from 0.1% to 40%, or from 0.5% to 20%, or from 1% to 15%, or from 7% to 20%, or from 8% to 19%, or from 10% to 18% monosaccharide. In at least one embodiment, the crosslinking agent is a pentose, tetraose, hexose, derivative thereof, or mixture thereof. Derivatives may be acetyl derivatives. In at least one embodiment, the sugar is an acetyl derivative of a monosaccharide.

In at least one embodiment, the fixing composition comprises a reducing sugar, and if the fixing composition is heated to a temperature of 100° C., the composition comprises from 1% to 20% reducing sugar. In at least one embodiment, the fixing composition comprises a reducing sugar and wherein, if the fixing composition is heated to a temperature of 100° C., the fixing composition comprises from 12% to 18% reducing sugar. In at least one embodiment, the fixing composition comprises sucrose, a buffering agent and a cosmetically acceptable carrier; and wherein, where the fixing composition is heated to a temperature of 100° C., the fixing composition comprises from 1% to 20% reducing sugar. Sucrose is able to break down into reducing sugar following heating. A similar effect is obtained with O-methyl glycosides, isopropylidenes, and benylidenes. In at least one embodiment, the crosslinking agent is a O-methyl glycoside, isopropylidene, or a benylidene. In at least one embodiment, the sugar is a glucoside. In at least one embodiment, the sugar is methyl glucoside. In at least one embodiment, the sugar is a disaccharide. In at least one embodiment, the sugar is sucrose. In at least one embodiment, the fixing composition comprises a reducing sugar. In at least one embodiment, the fixing composition comprises from 0.1% to 20.0%, or from 2% to 15%, or from 5% to 12% reducing sugar. In at least one embodiment, the fixing composition comprises from 12% to 18% reducing sugar. In at least one embodiment, the fixing composition comprises a total amount of reducing sugar being from 12% to 18% reducing sugar.

In at least one embodiment, the fixing composition comprises a reducing sugar and a cosmetically acceptable carrier. As used herein, the expression "reducing sugar" means any sugar that either has an aldehyde group or is capable of forming an aldehyde group in solution through isomerism, and that gives a positive result in the Benedict's test. An aldehyde group is —C(=O)H. The Benedict's test involves employment of the Benedict's solution. The Benedict's solution is available from Aldrich as 'Benedict's Reagent', which comprises sodium carbonate, copper sulphate pentahydrate and 2,5-difluorotoluene. In the Benedict's test, 1 mL of Benedict's solution is added to a 20 mL of 5% aqueous solution comprising a dissolved test compound. Benedict's solution contains blue copper(II) ions ($Cu^{2+}$). The solution is heated to 80° C. for 15 min and the resulting colour change is noted. The cupric ion of the Benedict's solution is reduced to cuprous ion by the aldehyde of the sugar. A positive test is confirmed with a change in colour as cupric ions ($Cu^{2+}$) are converted to cuprous ions i.e. reduced to copper(I) ions ($Cu^+$). These are precipitated as red copper(I) oxide which is insoluble in water. The test is also designed for longer heating time and higher temperature to note any colour change. The solution may range in colour (with increasing amounts of reducing sugar) from green, through yellow and orange, to red. Any colour change away from blue suggest levels of reducing sugar. The wavelength will change with the colour.

TABLE 1

Assessment of sugars using the Benedict's Test

| Sugar | 80° C., 15 min | 100° C., 40 min |
|---|---|---|
| Control (buffer solution*) | Negative | Negative |
| Ribose | Positive | Positive |
| Arabinose | Positive | Positive |
| Glucose | Positive | Positive |
| Fructose | Positive | Positive |
| Xylose | Positive | Positive |
| Sucrose | Negative | Positive |
| Methyl glucoside | Negative | Positive |

*Benedict's solution only.

In general, the Benedict's reagent is used as a test for the presence of reducing sugars. This includes all monosaccharides and many disaccharides, including lactose and maltose. Even more generally, Benedict's test will detect the presence of aldehydes, and alpha-hydroxy-ketones, including those that occur in certain ketoses. Thus, although fructose, a ketose, is not strictly a reducing sugar, it is an alpha-hydroxy-ketone, it gives a positive test because it is converted to the aldoses glucose and mannose by the base in the reagent. The copper sulphate in Benedict's solution reacts with reducing sugars. One litre of Benedict's reagent can be prepared from 100 g of anhydrous sodium carbonate, 173 g of sodium citrate and 17.3 g of copper(II) sulfate pentahydrate. Benedict's Reagent provides a quantitative test for reducing sugars along with qualitative test. The colour of the obtained precipitate gives an idea about the quantity of sugar present in the solution. A greenish precipitate indicates about 0.5% concentration; yellow precipitate indicates 1% concentration; orange indicates 1.5% and red indicates 2% or higher concentration. A positive result in the Benedict's test can be recognised for a compound by a 5% (weight/weight) solution of compound in water as a red colouring. The aldehyde group of the sugar allows the sugar to act as a reducing agent, for example in the Benedict's test.

In at least one embodiment, the reducing sugar is selected from the group consisting of: ribose, arabinose, xylose, lyxose, galactose, mannose, glucose, and mixtures thereof. In at least one embodiment, the reducing sugar is either ribose, arabinose, xylose or a mixture thereof. In at least one embodiment, the fixing composition comprises a reducing sugar and wherein the reducing sugar is selected from the group consisting of: arabinose, ribose, and mixtures thereof. In at least one embodiment, the sole reducing sugar is a pentose. In at least one embodiment, the sole reducing sugar is selected from the group consisting of: arabinose, ribose, and mixtures thereof. The reducing sugars arabinose, ribose, and mixtures thereof have the benefit of excellent straightening performance. By treating hair with reducing sugar and subsequent heat treatment as per the invention the treated hair becomes durably straight. Arabinose and ribose are 5 carbon sugars and these are found to have even better performance than sugars with other carbon numbers, such as 6 carbon and 7 carbon sugars. On the other hand, 6 carbon sugars are highly available and thus have economic advantages. In at least one embodiment, the fixing composition comprises a total amount of reducing sugar being from 12% to 18% reducing sugar, and wherein the fixing composition comprises arabinose.

In at least one embodiment, the crosslinking agent comprises a functional group selected from the group consisting of: —C(=O)—, —C(=O)—H, and —C(=O)—O—. In at least one embodiment, the crosslinking agent comprises at least two functional groups functional group selected from the group consisting of: —C(=O)—, —C(=O)—H, —OH, —NH$_2$, and —C(=O)—O—. In at least one embodiment, the crosslinking agent comprises at least two functional groups functional group selected from the group consisting of: —C(=O)—H, —OH, —NH$_2$. In at least one embodiment, the crosslinking agent is a carbonyl compound. In at least one embodiment, the crosslinking agent is an aldehyde. Aldehydes are useful in that they react with amino groups in keratin fibres. Since keratin fibres are polypeptides, available amino groups are common.

In at least one embodiment, the crosslinking agent conforms to the formula H$_2$N—(CH$_2$)n-C(=O)—H, wherein n is an integer from 2 to 10, or from 5 to 8, and isomers thereof. In at least one embodiment, the crosslinking agent conforms to the formula H$_3$C—C(=O)—(CH$_2$)n-C(=O)—CH$_3$, wherein n is an integer from 0 to 10, from 1 to 8, or from 2 to 7, and isomers thereof. In at least one embodiment, the crosslinking agent comprises a heterocyclic 5-member ring. In at least one embodiment, the crosslinking agent comprises a heterocyclic 5-member ring comprising nitrogen and oxygen atoms. In at least one embodiment, the crosslinking agent is a ketone. In at least one embodiment, the crosslinking agent is a dial, or a dial having an OH group. In at least one embodiment, the crosslinking agent is an oxazolidone. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, isomers thereof, derivatives thereof, and mixtures thereof. In at least one embodiment, the crosslinking agent is selected from the group consisting of: 3-(2-hydroxyethyl)-2-oxazolidinone, hexane-2,5-dione, butane-2,3-dione, ethanedial, 2-hydroxy-butanedial, 4-oxo-pentanoic acid, and mixtures thereof. In at least one embodiment, the crosslinking agent is selected from the group consisting of: 3-(2-hydroxyethyl)-2-oxazolidinone, hexane-2,5-dione, butane-2,3-dione, 2-hydroxy-butanedial, 2,3,4-trihydroxy-pentanedial, and mixtures thereof. In at least one embodiment, the crosslinking agent is selected from the group consisting of: butane-2,3-dione; 2-hydroxy-butanedial; 2,3,4-trihydroxy-pentanedial; and mixtures thereof. In at least one embodiment, the crosslinking agent is selected from the group consisting of: butane-2,3-dione; 2-hydroxy-butanedial; 2,3,4-trihydroxy-pentanedial; and mixtures thereof. 2-hydroxy-butanedial (CAS Registry Number: 7724-28-9) is commercially available from FCH Group, PO Box 438, 14017, Chernigiv, Ukraine (http://fchgroup.net/). 2,3,4-trihydroxy-pentanedial can be synthesized by the following procedure:

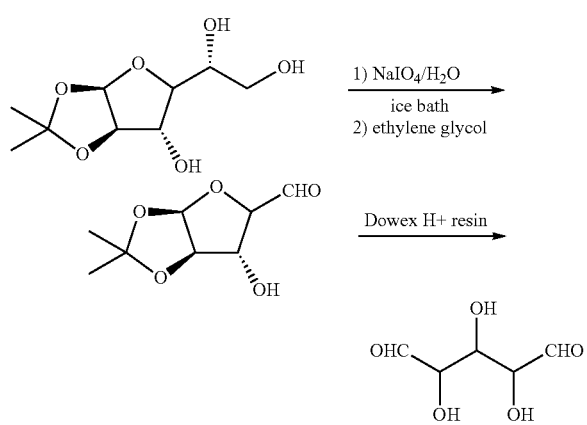

to a solution of 1,2-O-isopropylidene-D-glucofuranose (50 grams, 0.227 mol, CAS #185-40-1, Sigma-Aldrich) in water (500 mL) in an ice bath was added solid sodium meta periodate (50 grams, 0.183 mol, CAS #7790-28-5, Aldrich) portion wise over 30 minutes. The reaction was warmed to room temperature and stirred for 24 hrs. Ethylene glycol (5 mL) was added and the reaction was stirred for 3 hr at room temperature. The solution was then lyophilized overnight to remove water. The residue was dissolved in water (100 mL) and then extracted with chloroform (3×500 mL). The organic layers were combined, dried ($Mg_2SO_4$) and then the solvent was removed in vacuo to give a gummy, viscous oil. The gum was dissolved in water (200 mL), and treated with Amberlite H+ resin (5 grams; obtained from Rohm and Haas) at 70-80° C. for about 24 hrs. The reaction was cooled to room temperature, the resin was filtered off, and the filtrate was lyophilized to remove the water. The resulting off-white solid was stored in the freezer at 0° C. until testing. See also Horton D. et al (1970) *Carbohydrate Research*. 14 (2) p. 159-171 and also textbook "Methods in Carbohydrate Chemistry". Volume II. Page 320.

In at least one embodiment, the crosslinking agent comprises at least two functional groups selected from: —C(OH)— and —C(=O)OH. In at least one embodiment, the crosslinking agent is selected from the group consisting of: 1,2,4-butanetriol, oxobutanedioic acid, butanedioic acid, heptanedioic acid, 1,4-butanediol, 1,6-hexanediol, 1,2,6-hexanetriol, 6-amino-1-hexanol, 6-aminohexanoic acid, 2-aminobutanoic acid, ethane-1,2-diol, aminoethanoic acid, 2-hydroxyethanoic acid, 4-oxopentanoic acid, ethanedioic acid, aminooxoethanoic acid, and mixtures thereof. In at least one embodiment, the crosslinking agent is a diol conforming to the formula HO—$(CH_2)_n$-OH, wherein n is an integer from 2 to 12, or isomers thereof. In at least one embodiment, the crosslinking agent is a triol.

In at least one embodiment, the crosslinking agent comprises a —C(=O)OH functional group. Said carboxylic acid group has the advantage that the reaction with OH groups the kertain polypeptide is a more efficient reaction than other chemistries. In at least one embodiment, the crosslinking agent comprises a hydroxyl functional group. The hydroxyl group has the advantage that the crosslinking agent can further provide conditioning to the keratin fibres. In at least one embodiment, the crosslinking agent comprises both a —C(OH)— and a —C(=O)OH functional group. In at least one embodiment, the crosslinking agent conforms to the formula HO—$(CH_2)_n$-COOH, wherein n is an integer from 2 to 12, or from 4 to 10, or from 5 to 8, or isomers thereof. In at least one embodiment, the crosslinking agent conforms to the formula HOOC—$(CH_2)_n$-COOH, wherein n is an integer from 2 to 12, or from 4 to 10, or from 5 to 8, or isomers thereof. In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, and mixtures thereof. In at least one embodiment, the crosslinking agent further comprises a functional group selected from the group consisting of: —$NH_2$ and —C(=O)—. In at least one embodiment, the crosslinking agent is a triol and has 4 or more carbon atoms. In at least one embodiment, the fixing composition is substantially free of 2-hydroxypropane-1,2,3-tricarboxylic acid and propane-1,2,3-triol.

In at least one embodiment, the crosslinking agent is selected from the group consisting of: 1,4-butanediol, 1,6-hexanediol, 1,2,4-butanetriol, 1,2,6-hexanetriol, butanedioic acid, heptanedioic acid, 2-oxo-butanedioic acid, 6-amino-1-hexanol, 6-amino hexanoic acid, 2-aminobutanoic acid, 1,2-ethanediol, 2-aminoacetic acid, 2-hydroxy-acetic acid, 4-oxo-pentanoic acid, ethanedioic acid, 2-amino-2-oxo-acetic acid, and mixtures thereof. In at least one embodiment, the crosslinking agent is selected from the group consisting of: 1,2,4-butanetriol; oxobutanedioic acid; butanedioic acid; heptanedioic acid; 1,4-butanediol; 1,6-hexanediol; 1,2,6-hexanetriol; and mixtures thereof.

In at least one embodiment, the crosslinking agent is selected from the group consisting of: oxoethanoic acid, 2,2-dihydroxyethanoic acid, 2,2'-oxybis(2-hydroxy)-ethanoic acid, a derivative thereof, and mixtures thereof. In at least one embodiment, the crosslinking agent is 2,2-dihydroxyethanoic acid. In at least one embodiment, the active is a derivative of oxoethanoic acid, 2,2-dihydroxyethanoic acid, or 2,2'-oxybis(2-hydroxy)-ethanoic acid. Suitable derivatives are disclosed in WO02013/117771A1, which is incorporated herein by reference. In at least one embodiment, the active is a salt of oxoethanoic acid, 2,2-dihydroxyethanoic acid, 2,2'-oxybis(2-hydroxy)-ethanoic acid, or a mixture of two or more of said salts. In at least one embodiment, the derivative is selected from the group consisting of: methyl glyoxylate, ethyl glyoxylate, 2-hydroxyethyl glyoxylate, 3-hydroxypropyl glyoxylate, glyceryl glyoxylate, dihydroxyacetone glyoxylate, glyceryl diglyoxylate or triglyoxylate, sorbitol mono-, di- or triglyoxylate, glucose mono-, di- or triglyoxylate, 1,3-propanediol glyoxylate, 1,2-ethanediol glyoxylate, and mixtures thereof. In at least one embodiment, the derivative is selected from the group consisting of formulae 1 to 4 below, and mixtures thereof:

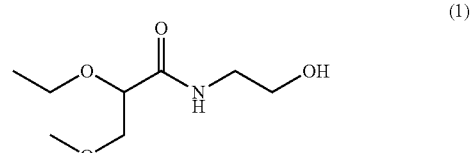

(1)

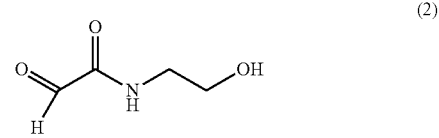

(2)

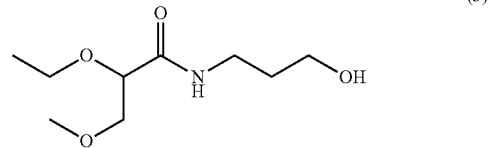

(3)

-continued

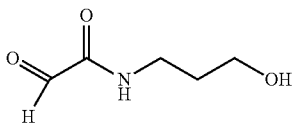
(4)

In at least one embodiment, the derivative is selected from the group consisting of formulae 1' to 6' below, and mixtures thereof:

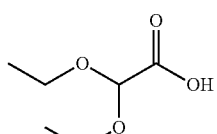
(1')

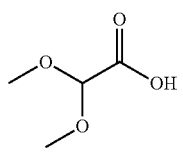
(2')

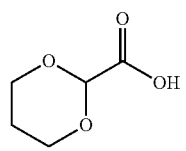
(3')

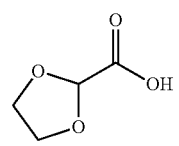
(4')

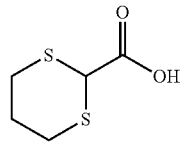
(5')

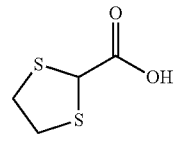
(6')

In at least one embodiment, the derivative is selected from the group consisting of formulae 1" to 5" below, and mixtures thereof:

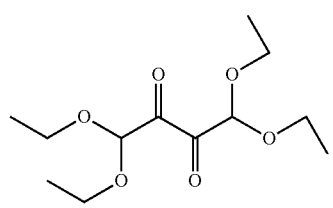
(1")

-continued

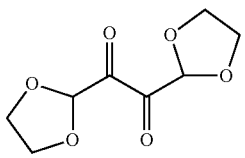
(2")

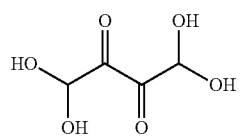
(3")

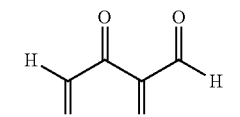
(4")

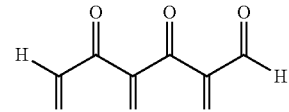
(5")

In at least one embodiment, the crosslinking agent is selected from the group consisting of: oxoethanoic acid, 2,2-dihydroxyethanoic acid, 2,2'-oxybis(2-hydroxy)-ethanoic acid, and mixtures thereof. In at least one embodiment, the crosslinking agent is a mixture of oxoethanoic acid, 2,2-dihydroxyethanoic acid, and 2,2'-oxybis(2-hydroxy)-ethanoic acid. In at least one embodiment, the crosslinking agent is 2,2-dihydroxyethanoic acid. Oxoethanoic acid and 2,2-dihydroxyethanoic acid are available from Sigma Aldrich.

In at least one embodiment, the crosslinking agent is selected from the group consisting of: 2-hydroxypropane-1, 2,3-tricarboxylic acid, 1,2,3,4-butanetetracarboxylic acid, a derivative thereof, and mixtures thereof. In at least one embodiment, the crosslinking agent is 2-hydroxypropane-1, 2,3-tricarboxylic acid. In at least one embodiment, the crosslinking agent is 1,2,3,4-butanetetracarboxylic acid. 2-hydroxypropane-1,2,3-tricarboxylic acid and 1,2,3,4-butanetetracarboxylic acid are available from Sigma Aldrich.

In at least one embodiment, the crosslinking agent is a carbonate ester. In at least one embodiment, the carbonate ester conforms to the formula $R_1O(C=O)OR_2$ wherein $R_1$ and $R_2$ are independently a $C_{1-18}$ alkyl, alkylene, or phenyl, which includes cyclic, non-cyclic, branched chain and straight chain. In at least one embodiment, the carbonate ester conforms to the formula $R_1O(C=O)OR_2$ wherein $R_1$ and $R_2$ are independently a $C_{1-10}$ alkyl or alkylene. In at least one embodiment, the carbonate ester conforms to the formula $R_1O(C=O)OR_2$ wherein $R_1$ and $R_2$ are independently selected from: methyl, ethyl, and phenyl. In at least one embodiment, the carbonate ester is selected from the group consisting of: 1,3-dioxolan-2-one; dimethyl carbonate; diethyl carbonate; diphenyl carbonate; 1,3-dioxan-2-one (trimethylene carbonate); 4-methyl-1,3-dioxolan-2-one; and mixtures thereof.

In at least one embodiment, the fixing composition further comprises a second crosslinking agent. The second crosslinking agent is useful for reacting with and providing further crosslinks in keratin. The hair comprises polypeptides of keratin having functional groups —COOH, OH, and $NH_2$, and SH. Different crosslinking agents can react preferentially with each functional group. For instance, arabinose preferentially reacts with amino groups whereas ethylene carbonate reacts preferentially with —COOH. In at least one embodiment, the second crosslinking agent is a sugar. Sugars are useful because they are naturally-derived, which is preferred by consumers versus synthetic compounds. This is not only for perceived health and lack of sensitisation reasons, but also for sustainability and environmental reasons—sugars break down naturally and quickly and do not require special disposal methods. Furthermore, sugars are also easy to source and relatively inexpensive. In at least one embodiment, the second crosslinking agent has a molecular weight of 500 g/mol or less. In at least one embodiment, the second crosslinking agent is one of the crosslinking agents mentioned above. In at least one embodiment, the second crosslinking agent has at least two functional groups selected from the group consisting of: —$NH_2$, —NH—, —SH, —OH, —C(=O)H, —C=O, and —COOH; and wherein the second crosslinking agent has a molecular weight of 500 g/mol or less. In at least one embodiment, the second crosslinking agent has a molecular weight of 300 g/mol or less, or from 50 g/mol to 250 g/mol, or from 80 g/mol to 150 g/mol. The molecular weight is useful in view of penetration into the keratin fibers to crosslink it from the inside and not just superficially where the crosslink is more exposed to external factors. In the context of keratin fibres, the molecular weight is useful for penetration into the hair shaft i.e. under the cuticle. In at least one embodiment, the second crosslinking agent is liquid at 25° C. Second crosslinking agents being liquid at this temperature have the advantage of providing improved hair feel versus second crosslinking agents that are solid at this temperature.

In at least one embodiment, the fixing composition has a pH of from pH 2 to pH 11. In at least one embodiment, the fixing composition has a pH of from pH 2 to pH 6.5, of from pH 3 to pH 5, or from pH 3 to pH 4. In at least one embodiment, the fixing composition has a pH of from pH 6 to pH 10. In at least one embodiment, the fixing composition has a pH of from pH 6.5 to pH 9.75, or from pH 7.0 to pH 9.5, or from pH 7.5 to pH 9.25, or from pH 8.0 to pH 9.0. In at least one embodiment, the fixing composition has a pH of from pH 6.5 to pH 9.75. A basic pH is useful in view of penetration into hair.

In at least one embodiment, the fixing composition comprises a buffering agent. In at least one embodiment, the buffering agent is a phosphate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia.

In at least one embodiment, the fixing composition comprises an antioxidant. An antioxidant is useful in view of providing longer-term stability for the composition. In at least one embodiment, the fixing composition comprises from 0.001% to 5%, or from 0.5% to 1.0% antioxidant. Suitable antioxidants are described below.

In at least one embodiment, the fixing composition comprises a chelator or chelating agent. In at least one embodiment, the fixing composition comprises a safe and effective amount of a chelator or chelating agent. In at least one embodiment, the fixing composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In at least one embodiment, the fixing composition comprises from 0.00001% to 10%, or from 0.001% to 5%, or from 0.001% to 5%, or from 0.5% to 1.0% chelating agent.

In at least one embodiment, the fixing composition comprises a hairstyling polymer. In at least one embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers are described below.

In at least one embodiment, the fixing composition comprises a photocatalyst. In at least one embodiment, the fixing composition comprises a photocatalyst being a hydroxy-substituted aromatic compound. A photocatalyst is an acid or base (or conjugate thereof) having a pKa (or pKb) value that decreases (or increases) upon exposure to electromagnetic radiation, particularly light. Photoacids are mentioned for example in Domcke and Sobolewski (2003), Unraveling the Molecular Mechanisms of Photoacidity, 302, p. 1693 and in Kowalewska (2005), *Photoacid catalyzed sol-gel process*, J. Mater. Chem. 15, p. 4997, which are both incorporated herein by reference. In at least one embodiment, the electromagnetic radiation is selected from the group consisting of: ambient light, sunlight, incandescent light, fluorescent light, LED light, laser light, and combinations thereof. In at least one embodiment, the electromagnetic radiation is selected from the group consisting of: visible light, near or far ultraviolet light, or near or far infrared light, and combinations thereof. In at least one embodiment, the photocatalyst can be activated to a photo-excited state by excitation with incident radiation with a wavelength from 300 nm to 750 nm and wherein the appliance emits radiation with a wavelength from 300 nm to 750 nm.

In at least one embodiment, the hydroxy-substituted aromatic compound is selected from the group consisting of: 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-brono-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, Pelargonidin, and mixtures thereof. In at least one embodiment, the hydroxy-substituted aromatic compound is selected from the group consisting of: 8-quinolinol-1-oxide, 8-hydroxyquinoline, 7-cyano-2-naphthol, 8-cyano-2-naphthol, 5-cyano-2-naphthol, and mixtures thereof. In at least one embodiment, the hydroxy-substituted aromatic compound is selected from the group consisting of: 8-quinolinol-1-oxide, 8-hydroxyquinoline, and mixtures thereof. In at least one embodiment, the hydroxy-substituted aromatic compound is 8-hydroxyquinoline. 8-hydroxyquinoline may act as a photoacid catalyst in lower pH solutions or as a photobase catalyst in higher pH solutions. 8-hydroxyquinoline has the CAS Number 148-24-3 and is available from Sigma-Aldrich. In at least one embodiment, the hydroxy-substituted aromatic compound is multi-cyclic. 8-hydroxyquinoline has the advantage of being easily available and characterised for use in cosmetic compositions such as hair dye compositions.

In at least one embodiment, the photocatalyst is selected from the group consisting of: sulfonated pyrene compounds, onium salts, diazomethane derivatives, bissulfone derivatives, disulfuno derivatives, nitrobenzyl sulfonate derivates, sulfonic acid ester derivatives, sulfonic acid esters of an N-hydroxyimide, glyoxime derivatives, and mixtures thereof. In certain other embodiments, the photocatalyst is 8-hydroxy-1,3,6-pyrentrisulfonic acid trisodium salt (D&C Green 8). In at least one embodiment of the alternative aspect, the photocatalyst is a photobase. Photobase catalysts may include derivatives of trityl alcohols such as, for example, Malachite green. Photobase catalysts may also include acridine derivatives such as, for example, 9-hydroxy-10-methyl-9-phenyl-9,10-dihydroacridine. Photobase catalysts may also include photoactive carbamate-containing compounds.

In at least one embodiment, the fixing composition comprises from 10 ppm to 500 ppm photocatalyst. The concentration of photocatalyst may dependent, in part, on a variety of factors including, for example, the chemical structure of the photocatalyst, the reaction medium, the reaction type, and the substrate. In at least one embodiment, the fixing composition comprises from 20 ppm to 500 ppm, or from 30 ppm to 450 ppm, or from 30 ppm to 400 ppm, or from 50 ppm to 350 ppm, or from 70 ppm to 330 ppm, or from 80 ppm to 310 ppm, or from 90 ppm to 300 ppm, or from 100 ppm to 290 ppm, or to 260 ppm, or to 250 ppm, or to 240 ppm, or to 220 ppm, or to 210 ppm, or to 200 ppm photocatalyst. To note: 1 ppm=1 parts per million=1×$10^{-4}$%=0.0001% and 10 ppm=1×$10^{-3}$%=0.001% and 100 ppm=1×$10^{-2}$%=0.01%.

In at least one embodiment, the fixing composition has not been exposed to electromagnetic radiation having a wavelength of 750 nm or less and for 30 min or more. The exposure of the fixing composition is important in view of the efficacy of the photocatalyst since when it is exposed to electromagnetic radiation within a certain wavelength range it will react with surround molecules if they are available, including compounds in the packaging wall. In at least one embodiment, the fixing composition is packaged in a container where electromagnetic radiation having a wavelength of 750 nm or less is not able to contact the fixing composition. In at least one embodiment, the fixing composition has not been exposed to electromagnetic radiation having a wavelength of 750 nm or less, or from 300 nm to 750 nm, or visible light, or UV light, and for 20 min or more, or 10 min or more, or 2 min or more. In at least one embodiment, the fixing composition is packaged in an opaque container. In at least one embodiment, the fixing composition is packaged in an amber- or brown-coloured container.

Compositions

The hair shaping method involves using a reducing composition and a fixing composition. Other compositions may be employed in addition. For brevity, the reducing composition, fixing composition and other compositions may be referred to herein, particularly hereinafter, as "composition".

In at least one embodiment, the composition comprises a cosmetically acceptable carrier. In at least one embodiment, the cosmetically acceptable carrier is any carrier suitable for formulating the reducing agent and/or reducing sugar into a composition being suitable for application onto hair. In at least one embodiment, the cosmetically acceptable carrier is selected from either an aqueous carrier or an aqueous-alcoholic carrier. In at least one embodiment, when the carrier is an aqueous-alcoholic carrier, which comprises water and an alcohol. In at least one embodiment, when the carrier is an aqueous carrier, this carrier consists essentially of water and is substantially free of alcohol. In at least one embodiment, the hair care composition comprises from 0.1% to 99%, or from 1% to 95%, or from 10% to 90%, or from 30% to 85% water.

In at least one embodiment, the composition comprises an antioxidant. An antioxidant is useful in view of providing longer-term stability for the composition. In at least one embodiment, the composition comprises from 0.001% to 5%, or from 0.5% to 1.0% antioxidant. In at least one embodiment, the antioxidant is selected from the group consisting of: sodium benzoate, ascorbic acid (vitamin C), ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, perborate, thioglycolates, persulfate salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, 1-methionine, proline, superoxide dismutase, silymarin, tea extracts, grape skin and/or grape seed extracts, melanin, rosemary extracts, and mixtures thereof. In at least one embodiment, the antioxidant is tocopherol sorbate or an ester of tocopherol. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee. In at least one embodiment, the antioxidant is sodium benzoate. In at least one embodiment, the antioxidant is ascorbic acid. Ascorbic acid has the benefit of enhancing the oxidative stability of the formulation.

In at least one embodiment, the composition comprises a chelator or chelating agent. As used herein, "chelator" or "chelating agent" means an crosslinking agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage, in order to decrease the local iron load, which generates, as indicated above, a pro-oxidant situation and pigmentation. In at least one embodiment, the composition comprises a safe and effective amount of a chelator or chelating agent. In at least one embodiment, the composition comprises a chelating agent, and wherein the chelating agent is selected from the group consisting of: N-hydroxysuccinimide, EDTA, NTA, deferoxamine, hydroxamic acids and their salts, phytic acid, phytate, gluconic acid and its salts, transferrine, lactoferrin, and mixtures thereof. In at least one embodiment, the composition comprises from 0.00001% to 10%, or from 0.001% to 5%, or from 0.001% to 5%, or from 0.5% to 1.0% chelating agent. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. In at least one embodiment, the chelating agent is selected from the group consisting of: N-hydroxysuccinimide deferoxamine, lactoferrin, hydroxamic acids, gluconic acid, phytic acid, derivatives thereof, and mixtures thereof.

In at least one embodiment, the composition comprises a hairstyling polymer. In at least one embodiment, the hairstyling polymer is selected from the group consisting of: non-ionic hairstyling polymer, anionic hairstyling polymer, zwitterionic and/or amphoretic hairstyling polymer, cationic hair styling polymer, or mixtures thereof. Suitable hairstyling polymers may be found in the CTFA International Cosmetics Ingredient Dictionary and Handbook, "Hair Fixatives", $12^{th}$ edition (2008). Suitable hairstyling polymers are, for example, those materials disclosed from page 12, line 5 to page 19, line 1 of the European patent application 08151246.9 filed on 11 Feb. 2008, which is incorporated herein by reference.

In at least one embodiment, the composition comprises from 0.01% to 10% by weight, or from 0.1% to 8%, or from 0.1% to 5% hairstyling polymer.

In at least one embodiment, the composition comprises a non-ionic hairstyling polymer. In at least one embodiment, the non-ionic hairstyling polymer is a natural or synthetic polymer. In at least one embodiment, the non-ionic hair styling polymers is a polymer obtained from the polymerisation of at least one type of monomer selected from: vinylpyrrolidone; vinylcaprolactam; vinyl esters; vinyl alcohol; vinyl acetate; (meth)acrylamide, and/or its derivatives; (meth)acrylic acid, its salts, and/or its derivatives; propylene and/or ethylene glycol acid; crotonic acid; or mixtures thereof. For example, such polymers are available under the trade names Luviskol® or Luviset Clear®.

In at least one embodiment, the composition comprises an anionic hairstyling polymer. In at least one embodiment, the anionic hairstyling polymer is selected from the group consisting of: acrylic acid/alkyl acrylate/Nalkylacrylamide terpolymer; vinyl acetate/crotonic acid copolymer; C1-C5-alkyl acrylate/(meth)acrylic acid copolymer; sodium polystyrenesulfonate; vinyl acetate/crotonic acid/vinyl alkanoate copolymer; vinyl acetate/crotonic acid/vinyl neodecanoate copolymer; aminomethylpropanol acrylate copolymer; vinylpyrrolidone/(meth)acrylic copolymer; methyl vinyl ether/maleic monoalkyl esters copolymer; aminomethylpropanol salts of allyl methacrylate/(meth)acrylate copolymer; ethyl acrylate/methacrylic acid copolymer; vinyl acetate/mono-nbutyl maleate/isobornyl acrylate copolymer; octylacrylamid/(meth)acrylic acid copolymer; polyesters of diglycol, cyclohexanedimethanol, isophthalic acid and sulfoisophthalic acid; and mixtures thereof.

In at least one embodiment, the composition comprises a zwitterionic or amphoteric hairstyling polymer. In at least one embodiment, the zwitterionic or amphoteric hairstyling polymer is selected from the group consisting of: alkylacrylamide/alkylaminoalkyl methacrylate/(meth)acrylic acid copolymers; copolymers which are formed from at least one first monomer type which has quaternary amine groups, and at least one second monomer type which has acid groups; copolymers of fatty alcohol acrylates, of alkylamine oxide methacrylate and at least one monomer chosen from acrylic acid and methacrylic acid; methacryloylethylbetaine/methacrylic acid and/or esters copolymers; polyquaternium-47; polyquaternium-43; oligomers or polymers, preparable from quaternary croton betaines or quaternary croton betaine esters; or mixtures thereof.

In at least one embodiment, the composition comprises a cationic hairstyling polymer. In at least one embodiment, the cationic hairstyling polymer is selected from the group consisting of homopolymers or copolymers where a quaternary nitrogen groups are present either in the polymer chain or as substituent on one or more of the cationic monomers. The monomers containing ammonium groups may be copolymerized with non-cationic monomers. Suitable cationic monomers may be unsaturated, free-radically polymerizable compounds which carry at least one cationic group, in particular ammonium-substituted vinyl monomers, such as, for example, trialkylmethacryloxyalkylammonium, trialkylacryloxyalkylammonium, dialkyldiallylammonium and quaternary vinylammonium monomers with cyclic, cationic nitrogen-containing groups, such as pyridinium, imidazolium or quaternary pyrrolidones, e.g. alkylvinylimidazolium, alkylvinylpyridinium, or alkylvinylpyrrolidone salts. The alkyl groups of these monomers are preferably lower alkyl groups, such as, for example, C1 to C7-alkyl groups, particularly preferably C1 to C3-alkyl groups. Suitable noncationic monomers may be selected from (meth)acrylamide, derivatives thereof; acrylate, its derivative thereof; vinylcaprolactone, vinylcaprolactam, vinylpyrrolidone, vinyl esters, vinyl alcohol, propylene glycol or ethylene glycol. For example, suitable cationic hairstyling polymers are available under the tradenames Gafquat 755 N; Gafquat 734; Gafquat HS 100; Luviquat HM 550; Merquat Plus 3300; Gaffix VC 713; Aquaflex SF 40.

In at least one embodiment, the composition comprises a cationic hairstyling polymer derived from a natural polymer. In at least one embodiment, the cationic hairstyling polymer derived from a natural polymer is derived from a natural polymer selected from the group consisting of: cationic derivatives polysaccharides such as cellulose, starch and/or guar; chitosan, its salts, and/or its derivatives; or mixtures thereof. For example, suitable conventional polymers are polyquaternium-4; polyquaternium-10; polyquaternium-24; guar hydroxypropyltrimonium chloride; chitosonium pyrrolidonecarboxylate, and mixtures thereof.

In at least one embodiment, the compositions are in a form suitable for application onto hair. In at least one embodiment, the composition is in the form of an emulsion, a solution, or dispersion. In at least one embodiment, when being in the form of an emulsion, said emulsion may be a water-in-oil emulsion, an oil-in-water emulsion, or a multiple emulsion. The composition may be a leave-in composition or a rinse-off composition.

In at least one embodiment, the composition is in a form selected from the group consisting of: a shampoo; a hair conditioning composition; and a hairstyling composition. When being a hairstyling composition, said composition may be a gel composition; a spray gel composition, optionally dispensed using a mechanical spray device and/or at least one propellant; a non-aerosol hairspray, optionally dispensed using a suitable mechanically operated spraying device; a foamable composition, optionally dispensed using devices for foaming; hair wax composition; hair lotion composition; hair cream composition; or combinations thereof. In at least one embodiment, the reducing composition is in the form of ampoules and the fixing composition is in the form of cream.

In at least one embodiment, the composition comprises at least one cosmetic hair treatment agent selected from conditioning agents, hair cleansing agents, or mixtures thereof.

In at least one embodiment, the composition comprises a conditioning agent, or a hair conditioning agent. The composition may comprise any suitable and conventional hair conditioning agents. The term "hair conditioning agent" herein means any cosmetically acceptable compound having a cosmetic effect on hair, such as providing gloss to hair, making hair more manageable, improving hair touch, improving combability and/or giving hair more volume. Suitable hair conditioning agents may be found in the CTFA International Cosmetics Ingredient Dictionary and Handbook, "Hair conditioning agents", $12^{th}$ edition (2008). In at least one embodiment, the hair conditioning agent is selected from the group consisting of: cationic surfactants, non-ionic surfactants, silicone compounds, organic oily conditioning agents, and mixtures thereof. Suitable hair conditioning agents are, for example, those materials disclosed from page 19, line 3 to page 27, line 33 of the European patent application 08151246.9 filed on 11 Feb. 2008, which is incorporated herein by reference.

In at least one embodiment, the conditioning agent is a cationic surfactant. In at least one embodiment, the cationic surfactant comprises amino or quaternary ammonium moieties. In at least one embodiment, the composition comprises from 0.05% to 3.5%, or from 0.1% to 3.0%, or from 0.5% to 2.5%, or from 1.0% to 2.0% cationic surfactant. In at least one embodiment, cationic surfactant is according to Formula II:

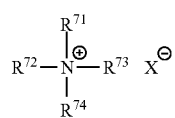

wherein at least one of $R^{71}$, $R^{72}$, $R^{73}$ and $R^{74}$ is selected from: an aliphatic group of from 8 to 30 carbon atoms; an aromatic, alkoxy, polyoxyalkylene, alkylamido, hydroxyalkyl, aryl; or an alkylaryl group having from 7 to 22 carbon atoms; wherein the remainder of $R^{71}$, $R^{72}$, $R^{73}$ and $R^{74}$ are independently selected from the group consisting of: an aliphatic group consisting of from 1 to 22 carbon atoms; and an aromatic, alkoxy, polyoxyalkylene, alkylamido, hydroxyalkyl, aryl or alkylaryl group having up to 22 carbon atoms; wherein X is selected from the group consisting of: halogen, acetate, citrate, lactate, glycolate, phosphate, nitrate, sulfonate, sulfate, alkylsulfate, alkyl sulfonate radicals, and mixtures thereof.

In at least one embodiment, cationic surfactant is according to Formula II (see above), wherein at least one of $R^{71}$, $R^{72}$, $R^{73}$ and $R^{74}$ is an aliphatic group having from 16 to 24 carbon atoms; wherein the remainder of $R^{71}$, $R^{72}$, $R^{73}$ and $R^{74}$ are independently selected from the group consisting of aliphatic groups having from 1 to 4 carbon atoms; wherein X is selected from the group consisting of: chloride or sulfate.

In at least one embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group.

In at least one embodiment, the cationic surfactant is selected from the group consisting of: behenyltrimethylammonium chloride, methyl sulfate or ethyl sulfate; stearyltrimethylammonium chloride, methyl sulfate or ethyl sulfate; and mixtures thereof. It is believed that a longer alkyl group provides improved smoothness and soft feeling on wet and dry hair, compared to cationic surfactants with a shorter alkyl group. It is also believed that such cationic surfactants can provide reduced scalp irritation, compared to those having a shorter alkyl group.

In at least one embodiment, the cationic surfactant is a di-long alkyl quaternized ammonium salt selected from the group consisting of: dialkyl (14-18 carbons) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In at least one embodiment, the cationic surfactant is a tertiary amidoamine having an alkyl group of from 12 to 22 carbons.

In at least one embodiment, the cationic surfactant is selected from the group consisting of: cetyl trimethyl ammonium salts; behenyl trimethyl ammonium salts; dimethyl ditallow ammonium salts; stearyl amidopropyl dimethylamine; (di)esterquats; quaternium 8, 14, 15, 18, 22, 24, 26, 27, 30, 33, 37, 53, 60, 61, 72, 78, 80, 81, 82, 83, 84, and/or 91; or mixtures thereof.

In at least one embodiment, the conditioning agent is a non-ionic surfactant. Suitable non-ionic surfactants may be surfactants having a HLB of less than 8. Suitable nonionic surfactants may be selected from glyceryl esters; sugar esters; alkylpolyglucoside ethers; oleyl- or isostearylpolyglucoside; polyoxyethylene (20) sorbitan monostearate; or mixtures thereof.

In at least one embodiment, the conditioning agent is a silicone compound. In at least one embodiment, the silicone compound is volatile or nonvolatile, and/or soluble or insoluble silicones. For example, suitable silicone conditioning agents are available under the tradenames SF 1075 methyl phenyl fluid (Electric company); DC200 Fluid, DC244, DC245, DC345, Dow 5-7113, DC556 Cosmetic Grade Fluid, DC1248 (Dow Corning). In at least one embodiment, the composition comprises a conditioning agent being the reaction product of: (a) an aminosilane; (b); polysiloxane; and optionally (c) a polyether. In at least one embodiment, the composition comprises a conditioning agent being the reaction product of: (a) an aminosilane; (b); polysiloxane; and (c) a polyether. In at least one embodiment, the composition comprises a conditioning agent being the reaction product of: (a) an aminosilane; (b) polysiloxane; and (c) a polyether; and optionally (d) an amine. In at least one embodiment, the polysiloxane is an epoxy encapped polysiloxane. In at least one embodiment, the polysiloxane comprises at least two oxirane or oxetane groups. In at least one embodiment, the polysiloxane comprises from 10 to 450 silicon atoms, or from 40 to 400 silicon atoms, from 75 to 350 silicon atoms, from 150 to 250 silicon atoms. In at least one embodiment, the polysiloxane is an epoxy encapped polysiloxane. In at least one embodiment, the polyether has the average structure $CH_2(O)CHCH_2O(CH_2(CH_3)CH_2O)_n$ $CH_2CH(O)CH_2$ wherein n is an integer from 1 to 10. In at least one embodiment, the amine comprises from 1 to 10 carbon atoms, or from 2 to 5 carbon atoms. In at least one embodiment, the amine is an alkylamine that is substituted with at least one alkyl group. In at least one embodiment, the amine is selected from the group consisting of: methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2,3,3,4,4,5,5,6,6,7,7,8,8,8-pentadecafluoro-1-octanamine, and mixtures thereof. In at least one embodiment, the amine is selected from the group consisting of: methylethylamine, methylhexylamine, methyloctadecylamine, diethanolamine, dibenzylamine, dihexylamine dicyclohexylamine, piperidine, pyrrolidine phthalimide, and mixtures thereof. In at least one embodiment, the conditioning agent is an epoxyaminosilane copolymer. In at least one embodiment, the conditioning agent is conditioning agent being the reaction product of: (a) an aminosilane; (b) polysiloxane, wherein the polysiloxane comprises from 10 to 450 silicon atoms, or from 40 to 400 silicon atoms; and (c) a polyether; and (d) an amine, wherein the amine is an alkylamine that is substituted with at least one alkyl group. Epoxyaminosilane copolymers are described in EP2214633B1 (filing date 30 Oct. 2008, which is incorporated herein by reference) and are available from Momentive™ Performance Materials Inc., Columbus, Ohio, USA. Epoxyaminosilane copolymers have excellent durability benefits. Such an exemplary expoxyaminosilane copolymer may be synthesised as follows: aminopropyltriisopropoxy silane (40.77 g), an epoxy encapped polysiloxane with the average structure $CH_2(O)CHCH_2OCH_2CH_2Si(CH_3)_2O[Si(CH_3)_2O]_{50}Si(CH_3)_2CH_2CH_2CH_2OCH_2CH(O)CH_2$ (171.40 g) and an epoxy endcapped polyether with the average structure $CH_2(O)CHCH_2O(CH_2(CH_3)CH_2O)_7CH_2CH(O)CH_2$ (37.83 g) and isopropanol (425.68 g) is combined in a 500 mL flask. The material is brought to reflux and stirred with an overhead stirrer. The refluxing continued for 15.5 hr until all epoxy groups are consumed as determined by titration. The material is transferred to a rotary evaporator and stripped at 70° C. and 532 Pa (4 torr) for 2 hrs to remove the isopropanol. Another exemplary expoxyaminosilane copolymer may be synthesised as follows: aminopropyltriisopropoxy silane (14.27 g), 3-(diethylamino)propylamine (7.05 g), an epoxy encapped polysiloxane with the average structure $CH_2(O)CHCH_2OCH_2CH_2CH_2Si(CH_3)_2O[Si(CH_3)_2]_{200}Si(CH_3)_2CH_2CH_2CH_2OCH_2CH(O)CH_2$ (447.87 g) and an epoxy encapped polyether with the average structure $CH_2(O)CHCH_2O(CH_2CH_2O)_{14}CH_2CH(O)CH_2$ (30.81 g) and isopropanol (500 g) is combined in a 2000 mL flask. The material is brought to reflux and stirred with an overhead stirrer. The refluxing continued for 24 hr until all epoxy groups are consumed as determined by titration. The material is transferred to a rotary evaporator and stripped at 70° C. and 532 Pa (4 torr) for 2 hrs to remove the isopropanol.

In at least one embodiment, the conditioning agent is selected from the group consisting of: epoxyaminosilane copolymers, and polysiloxane/polyurea block copolymers, and mixtures thereof. A polysiloxane/polyurea block copolymer is described in EP2074986B1 filed on 10 Dec. 2008, which is incorporated herein by reference. In at least one embodiment, the polysiloxane/polyurea block copolymer comprises at least one polysiloxane sequence (or block) and at least one polyurea sequence (block) in the backbone of the copolymer. In at least one embodiment, the amount of polysiloxane present in the copolymer is greater than 90% by weight relative to the total weight of the polysiloxane/polyurea block copolymer. In at least one embodiment, the polysiloxane/polyurea block copolymer of the does not comprise polyurethane. By way of non-limiting example, the copolymer can be a non-ionic polysiloxane/polyurea copolymer, that is to say that it does not comprise an ionized or ionizable group. By way of example of a copolymer, non-limiting mention may be made of the dimethylpolysiloxane/polyurea block copolymer having the INCI name polyureadimethicone. Such a dimethylpolysiloxane/polyurea block copolymer can be obtained, for instance, by copolymerization of an a,w-aminosilicone with a diisocyanate. Polysiloxane/polyurea block copolymers corresponding to these characteristics are, for example, the products sold under the reference Wacker-Belsil® UD 60, Wacker-Belsil® UD 80, Wacker-Belsil® DU 140 and Wacker-Belsil® UD 200 by Wacker. In at least one embodiment, the polysiloxane/polyurea copolymer is non-ionic. In at least one embodiment, the composition comprises from 0.05 to 20%, for example from 0.1 to 15%, or from 0.5 to 10% polysiloxane/polyurea block copolymer.

In at least one embodiment, the conditioning agent is an organic oily conditioning agent. In at least one embodiment, the organic oily conditioning agent is non-volatile, water-insoluble, oily or fatty. Organic oily conditioning agents may be selected from hydrocarbon oils and fatty esters.

In at least one embodiment, the conditioning agent is a fatty alcohol. In at least one embodiment, the fatty alcohol is a non-volatile low melting point fatty alcohol. In at least one embodiment, the conditioning agent is a fatty alcohol and the fatty alcohol is selected from the group consisting of: capryl alcohol, lauryl alcohol, stearyl alcohol, cetyl alcohol, myristyl alcohol, palmitoleyl alcohol, and mixtures thereof.

In at least one embodiment, the composition comprises at least one direct hair dye. In at least one embodiment, the composition comprises from 0.01% to 15%, or from 0.1% to 10%, or from 0.5% to 8% direct hair dye.

In at least one embodiment, the composition comprises a viscosity-modifying substance. In at least one embodiment, the composition comprises from 0.01% to 20%, or from 0.05% to 10%, or from 0.1% to 5% viscosity-modifying substance.

In at least one embodiment, the composition comprises at least one emulsifier and/or surfactant not being a hair conditioning agent. In at least one embodiment, the emulsifier and/or surfactant is selected from nonionic surfactants; anionic surfactants; amphoretic surfactants; or mixtures thereof. In at least one embodiment, the composition comprises from 0.01% to 20%, or from 0.05% to 10%, or from 0.1% to 5%, emulsifier and/or surfactant.

In at least one embodiment, the composition comprises at least one pigment. In at least one embodiment, the pigment is selected from natural pigments; synthetic pigments; or mixtures thereof. The pigments may be selected from organic pigment, inorganic pigment; or mixtures thereof. The pigments may be selected from coloured pigments; pearlescent pigments; or mixtures thereof. The composition may comprise from 0.01% to 10%, or from 1% to 2% pigment present in the product mass in undissolved form by weight of the total composition. The composition may comprise pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names.

In at least one embodiment, the composition comprises at least one particulate substance. In at least one embodiment, the particulate substance is selected from silica; silicates;

aluminates; clay earths; mica; insoluble salts, particularly insoluble inorganic metal salts; metal oxides; minerals; insoluble polymer particles; or mixtures thereof. In at least one embodiment, the composition comprises from 0.01% to 10%, or from 0.05% to 5% of at least one particulate substance.

In at least one embodiment, the composition comprises at least one photoprotective substance. In at least one embodiment, the composition comprises from 0.01% to 10%, or from 0.1% to 5%, or from 0.2% to 2% photoprotective substance.

In at least one embodiment, the composition comprises at least one preservative. In at least one embodiment, the composition may comprise from 0.01% to 5% by weight, or from 0.05% to 1% preservative.

A variety of additional optional ingredients may be incorporated into the composition of the present invention. Non-limiting examples of these additional ingredients may be selected from preservatives; antioxidants; sequestering agents; solvents; fragrances & perfumes; fillers; screening agents; odor absorbers; colouring materials; lipid vesicles; detersive surfactants; thickening agents and suspending agents; viscosity modifiers; pearlescent aids; UV-filters and sunscreens; agents for combating free radicals; polyvinyl alcohol; pH adjusting agents; salts; colouring agents; polymer plasticizing agents; direct dyes; or mixtures thereof. The composition may comprise from 0%, or from 0.1% to 5% antimicrobial agents. In at least one embodiment, the composition comprises an organic acid selected from the group consisting of: glycine, L-methionine, L-arginine, biotin, creatine, and mixtures thereof. In at least one embodiment, the composition comprises an antidandruff agent. In at least one embodiment, the composition comprises zinc pyrithione. In at least one embodiment, the composition comprises panthenol. In at least one embodiment, the composition comprises a wax compound. In at least one embodiment, the composition comprises beeswax.

In at least one embodiment, the composition has a viscosity, measured at 25° C., of from 0.1 mPa·s to 1,000,000 mPa·s, or from 1 mPa·s to 80,000 mPa·s, or from 5 mPa·s to 3,500 mPa·s. The viscosity is measured by HAAKE Rotation Viscometer VT 550 with cooling/heating vessel and sensor systems according to DIN 53019 (MV-DIN, SV-DIN), shear rate is 12.9 s$^{-1}$.

In at least one embodiment, the composition is substantially free of: formaldehyde, methylene glycol, formalin, and any compound that produces formaldehyde upon heating. "Heating" here means raising the temperature of the compound above 25° C. In at least one embodiment, the composition comprises 0% formaldehyde. In at least one embodiment, the composition is substantially free of: formaldehyde, 1,3,5-trioxane, paraformaldehyde, methylene glycol, formalin. Formaldehyde is not preferred in view of its safety profile. Methylene glycol and formalin are not preferred because formalin is a derivative of formaldehyde. Formaldehyde exists in multiple forms. In water, formaldehyde becomes hydrated and forms methylene glycol. A saturated solution of formaldehyde (about 40% formaldehyde) in water is more commonly known as formalin. Methanol and/or methylene diol can be used as a stabilizer in formalin.

In at least one embodiment, the composition has a pH of from pH 2 to pH 11. In at least one embodiment, the composition has a pH of from pH 6 to pH 10. In at least one embodiment, the composition has a pH of from pH 6.5 to pH 9.75, or from pH 7.0 to pH 9.5, or from pH 7.5 to pH 9.25, or from pH 8.0 to pH 9.0. In at least one embodiment, the composition comprises a buffering agent. In at least one embodiment, the buffering agent is a phosphate buffer. In at least one embodiment, the buffering agent is selected from the group consisting of: glycine/sodium hydroxide; sodium carbonate/sodium hydrogen carbonate, sodium tetraborate/sodium hydroxide; sodium bicarbonate/sodium hydroxide; ammonium chloride/ammonia. In at least one embodiment, the composition comprises an alkalizing agent and/or an agent for adjusting the pH value. The composition may further comprise a protonating agent. The protonating agent may be a monoprotic or polyprotic acid, water-soluble or water-insoluble acid, and/or an organic or inorganic acid. In at least one embodiment, the protonating agent is selected from formic acid, acetic acid, sulfuric acid, hydrochloric acid, citric acid, and mixtures thereof.

Method

The first aspect relates to a method for shaping keratin fibres. In at least one embodiment, the keratin fibres is hair, or human hair. In at least one embodiment, the method is for straightening or relaxing hair. In at least one embodiment, the method is for curling or perming hair. In at least one embodiment, the method is for mechanically shaping keratin fibres. In at least one embodiment, the mechanical shaping of keratin fibres is selected from the group consisting of: straightening keratin fibres, such as human scalp hair or human eyelashes, and curling keratin fibres, such as human scalp hair or human eyelashes.

In at least one embodiment, the reducing composition and/or the fixing composition is/are applied on wet hair and/or on dry hair.

The method does not use an oxidising agent, preferably does not use peroxide. The oxidising agent is capable of re-oxidising cysteine residues into disulfide bonds in keratin fibres. In at least one embodiment, the method does not use a peroxide compound. In at least one embodiment, the method does not use hydrogen peroxide. In at least one embodiment, the method does not use salicylic acid.

The keratin fibres are not rinsed between or during steps (c) to (e). In at least one embodiment, the keratin fibres are not rinsed after the fixing composition is applied. It is not advantageous to employ a rinsing after step (c) because less shaping durability is observed. Indeed, it is believed that reduced penetration into the hair shaft exists when the sugar molecules are rinsed off after step (c).

In at least one embodiment, the method does not use any coating material. In at least one embodiment, the method does not use any coating material selected from film coating material and sheet coating material. In at least one embodiment, the method does not use any coating means. Examples of film coating material or sheet coating material include plastic films, metal (foil) films. In at least one embodiment, method does not employ any: plastic film; foil; flexible heating film. Examples of such coating films and coating materials are disclosed in claim 1 and the examples of WO2011/074143A1, which published on 23 Jun. 2011. Indeed, such coating means is not preferred in view of the effect of such occlusive material in forming a condensation cage in which the cosmetically acceptable carrier a component or components in the composition may evaporate from the keratin fibers, adhere to the wall of the coating means, and drop onto the keratin fibers". In at least one embodiment, the method does not employ placing the keratin fibers in an occlusive space. "Film coating material" and "coating means" does not include liquid coating materials/means that then dry onto the hair. Examples of such liquid coating materials/means includes hairstyling polymers which are sometimes referred to as film-forming polymers.

In at least one embodiment, prior to step (a) the hair is washed with a shampoo, for example a cleansing shampoo. In at least one embodiment, following step (e) the hair is washed with a shampoo, for example a cleansing shampoo. In at least one embodiment, following step (e) the hair is washed with a shampoo, for example a cleansing shampoo, and subsequently conditioned with a conditioning formulation comprising a conditioning agent. Conditioning agents are disclosed herein.

In at least one embodiment, the molar ratio of reducing agent to crosslinking agent is from 2:1 to 1:10, or from 1:1 to 1:5.

Applying a Composition to Keratin Fibres

The present invention relates to a hair straightening and/or hair relaxing method comprising: (a) applying a reducing composition to keratin fibres. In at least one embodiment, applying a reducing composition to keratin fibres involves applying onto keratin fibres from 0.01 gram to 5 gram of said composition per gram keratin fibres.

The present invention relates to a hair straightening and/or hair relaxing method comprising: (c) applying a fixing composition to the hair. In at least one embodiment, applying a fixing composition to hair involves applying onto hair from 0.01 gram to 5 gram of said composition per gram hair.

In at least one embodiment, the fixing composition remains on the keratin fibres for a time X, wherein time X is from 2 min to 60 min, or from 5 min to 30 min.

In at least one embodiment, the fixing composition comprises: (i) a crosslinking agent, wherein the crosslinking agent has at least two functional groups selected from the group consisting of: $-NH_2$, $-NH-$, $-SH$, $-OH$, $-C(=O)H$, $-C=O$, and $-COOH$; and wherein the crosslinking agent has a molecular weight of 500 g/mol or less; (ii) a photocatalyst being a hydroxy-substituted aromatic compound; (iii) a cosmetically acceptable carrier; wherein the fixing composition has not been exposed to electromagnetic radiation having a wavelength of 750 nm or less for 30 min or more.

In at least one embodiment, the fixing composition is formed on the keratin fibres rather than provided prior to applying to keratin fibres. For example, a fixing formulation comprising the crosslinking agent and a cosmetically acceptable carrier is applied to the keratin fibres and then subsequently, a photocatalyst formulation comprising the photocatalyst is applied to the keratin fibres.

Rinsing the Keratin Fibres

In at least one embodiment, (b) involves rinsing the keratin fibres. In at least one embodiment, the keratin fibres are rinsed for 1 min to 60 min in flowing water, or from 5 min to 30 min, or to 10 min. In at least one embodiment, (f) involves rinsing the keratin fibres. In at least one embodiment, the keratin fibres are rinsed for 1 min to 60 min in flowing water, or from 5 min to 30 min, or to 10 min.

Drying the Keratin Fibres

The method comprises (d) drying the keratin fibres. In at least one embodiment, (d) is carried out by a blow drier. In at least one embodiment, (d) is carried out for a duration of from 1 min to 45 min, or from 2 min to 20 min, or from 5 min to 15 min. In general, following the hair drying, the hair can still be damp, but needs to have reasonable e.g. 75% hair fibre separation of the head of hair. Some residual moisture in the hair is acceptable.

In at least one embodiment, the drying is carried out by a hood device. In at least one embodiment, the drying is carried out by towelling hair and/or by pressing hair with hands.

Hair dryer or blow dryer distances between device and head are typically down to 10 cm. Blow dryers direct hot air through some sort of attachment for combing or otherwise treating the hair. A Blow dryer is typically used such that the distance to the hair (for example at a distance of 20 or 30 or 40 centimetres) and often is used with the aid of a comb or a brush. In at least one embodiment, the hair drying is carried out by a blow drier at a temperature of from from 50° C. to 100° C. In at least one embodiment, the hair drying is carried out by a blow drier at a temperature of up to 130° C.

Treating the Keratin Fibres with a Shaping Appliance

The method comprises (e) treating the keratin fibres with a shaping appliance. In at least one embodiment, the shaping appliance is selected from the group consisting of: hair straightening appliances, hair curling appliances, combing appliances and brushing appliances. In at least one embodiment, the appliance is a hair straightening appliance comprising a heating element. In at least one embodiment, the appliance is a hair curling appliance comprising a heating element. In at least one embodiment, the appliance is a hair straightening appliance comprising a heating element and a source of electromagnetic radiation for exposing hair to electromagnetic radiation. In at least one embodiment, the appliance is a combing or brushing appliance and the fixing composition is exposed to electromagnetic radiation having a wavelength of from 300 nm to 750 nm using a separate source of electromagnetic radiation such as a lamp. In at least one embodiment, the appliance comprises light-emitting diodes.

In at least one embodiment, method comprises (e) providing a shaping appliance at a temperature of from 100° C. to 280° C. and mechanically shaping the keratin fibres with the appliance. In at least one embodiment, the temperature is from 110° C. to 250° C., or from 120° C. to 240° C., or from 140° C. to 230° C., or from 160° C. to 220° C., or from 180° C. to 210° C., or from 190° C. to 200° C. In at least one embodiment, method comprises (e) providing a straightening appliance at a temperature of from 100° C. to 280° C. and mechanically straightening the keratin fibres with the appliance.

In at least one embodiment, the hair straightening appliance comprises metal or ceramic plates. In at least one embodiment, the metal or ceramic plates are provided to a temperature of from 100° C. to 280° C. In at least one embodiment, the metal or ceramic plates are provided to a temperature of from 110° C. to 250° C., or from 120° C. to 240° C., or from 140° C. to 230° C., or from 160° C. to 220° C., or from 180° C. to 210° C., or from 190° C. to 200° C. In at least one embodiment, the 'mechanically straightening the hair with the appliance' is carried out for a duration of from 1 min to 45 min, or from 2 min to 20 min, or from 5 min to 15 min.

In at least one embodiment, the 'mechanically straightening the hair with the appliance' is carried out by hair straightening appliance. In at least one embodiment, the hair straightening appliance comprises metal or ceramic plates. In at least one embodiment, the hair straightening appliance are straightening irons. Hair straightening appliances comprising metal or ceramic plates, such as straightening irons typically rely on resistive heating, but heat is not transported through hot air, but by direct contact with the keratin fibres i.e. hair. The direct contact is often made by bringing the hair in contact with some metal or ceramic surface of the appliance. These devices are not or at least not primarily used to dry the hair. Rather are they used to change the hair style, typically either to create curls or to straighten hair. The surfaces meant for hair contact (e.g. metal or ceramic plates)

of these devices typically reach temperatures from 130° C. to 250° C. Most devices have metal or ceramic plates used with temperatures from 160° C. to 230° C.

U.S. Pat. No. 5,612,849 and U.S. Pat. No. 6,191,930 disclose a heat generating hair care appliance in the form of a hot air hair care appliance. The respective devices are typically referred to as hair dryers or blow dryers. USD383245 discloses another heat generating hair care appliance in the form of a hot air hair care appliance. The respective devices are typically referred to as hot air stylers or hair stylers. US2008/0196739 discloses a heat generating hair care appliance in the form of a hot surface hair care appliance, typically referred to as straightening irons.

In at least one embodiment, the fixing composition and/or keratin fibres are exposed to electromagnetic radiation having a wavelength of from 300 nm to 750 nm. In at least one embodiment, the electromagnetic radiation has a wavelength of from 310 nm, or from 320 nm, or from 330 nm, or from 340 nm, or from 350 nm, or from 360 nm, or from 370 nm, or from 380 nm, or from 390 nm, or from 400 nm, or from 410 nm, to 740 nm, or to 730 nm, or to 720 nm, or to 710 nm, or to 700 nm, or to 690 nm, or to 680 nm, or to 670 nm, or to 650 nm, or to 640 nm. In at least one embodiment, the electromagnetic radiation has a wavelength of from 380 nm to 550 nm.

In at least one embodiment, the electromagnetic radiation is selected from the group consisting of: ambient light, sunlight, incandescent light, fluorescent light, LED light, laser light, and combinations thereof. In at least one embodiment, the electromagnetic radiation is selected from the group consisting of: visible light, near or far ultraviolet light, or near or far infrared light, and combinations thereof. In at least one embodiment, the electromagnetic radiation is light. In at least one embodiment, the suitable light may be provided from any source capable of illuminating the substrate surface. In at least one embodiment, the light is selected from the group consisting of: ambient sunlight, incandescent light, and fluorescent light. In at least one embodiment, the light is provided by conventional sources such as lamps and portable or battery-powered lights. Specific devices may be developed or adapted for use with the fixing compositions and method described herein. In at least one embodiment, the appliance is a hair brush configured to incorporate LEDs In at least one embodiment, the light is laser light. Laser may be used to provide precise targeting, for example. In at least one embodiment, the appliance is hybrid heat- and light-providing hair shaping irons. Suitable irons are disclosed in CN201504727U.

Irradiance, that is the power of electromagnetic radiation in Watts per unit area, has the unit Watts per $m^2$ or $W/m^2$. Irradiance is thus a measurement of the intensity of electromagnetic radiation. Light intensity can also be measured in lux (lx), which is the unit of illuminance. 1 lx=about $1.5 \times 10^{-7}$ $W/cm^2$ (at 555 nm). An average laboratory or office space would have a light intensity of about 200 lx to about 1000 lx i.e. an irradiance of about $2.9-10^{-5}$ $W/cm^2$ to about $1.4 \times 10^{-4}$ $W/cm^2$ (at 555 nm). In at least one embodiment, the electromagnetic radiation has an irradiance of at least $1 \times 10^{-3}$ $W/cm^2$, or at least $5 \times 10^{-3}$ $W/cm^2$, or at least $1 \times 10^{-2}$ $W/cm^2$, or at least $5 \times 10^{-2}$ $W/cm^2$, or at least $1 \times 10^{-1}$ $W/cm^2$, or at least $5 \times 10^{-1}$ $W/cm^2$. In at least one embodiment, the electromagnetic radiation has an illuminance of at least 1000 lx, or at least 2000 lx, or at least 3000 lx, or at least 4000 lx, or at least 5000 lx, or at least 6000 lx, or at least 7000 lx, or at least 8000 lx, or at least 9000 lx, or at least 10000 lx, or at least 20000 lx, or at least 30000 lx, or at least 40000 lx, or at least 50000 lx, or at least 60000 lx, or at least 70000 lx, or at least 80000 lx.

$2^{nd}$ Aspect

According to a second aspect, the present invention relates to the use of a fixing composition for oxidising cysteine residues into disulphide bonds; wherein the fixing composition comprises a crosslinking agent; wherein the crosslinking agent has at least two functional groups selected from the group consisting of: —NH$_2$, —NH—, —SH, —OH, —C(=O)H, —C=O, and —COOH; and wherein the crosslinking agent has a molecular weight of 500 g/mol or less. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, ribose, arabinose, xylose, lyxose, galactose, mannose, 3-(2-hydroxyethyl)-2-oxazolidinone, hexane-2,5-dione, butane-2,3-dione, ethanedial, 2-hydroxy-butanedial, 4-oxo-pentanoic acid, 1,4-butanediol, 1,6-hexanediol, 1,2,4-butanetriol, 1,2,6-hexanetriol, butanedioic acid, heptanedioic acid, oxoethanoic acid, 2,2-dihydroxyethanoic acid, 2,2'-oxybis(2-hydroxy)-ethanoic acid, 2-hydroxypropane-1,2,3-tricarboxylic acid, 1,2,3,4-butanetetracarboxylic acid, 1,3-dioxolan-2-one, dimethyl carbonate, diethyl carbonate, diphenyl carbonate; 1,3-dioxan-2-one, 4-methyl-1,3-dioxolan-2-one, and mixtures thereof. In at least one embodiment, the crosslinking agent is a reducing sugar.

$3^{rd}$ Aspect

According to the third aspect, the present invention relates a kit comprising:
  a reducing composition, wherein the reducing composition comprises a reducing agent;
  a fixing composition, wherein the fixing composition comprises a comprises a crosslinking agent; wherein the fixing composition comprises a crosslinking agent; wherein the crosslinking agent has at least two functional groups selected from the group consisting of: —NH$_2$, —NH—, —SH, —OH, —C(=O)H, —C=O, and —COOH; and wherein the crosslinking agent has a molecular weight of 500 g/mol or less;
  optionally an appliance for mechanically shaping hair.

In at least one embodiment, the compositions of the kit are comprised in a multi-compartment device. In at least one embodiment, the appliance is hair straightening irons. In at least one embodiment, the crosslinking agent is selected from the group consisting of: 1,7-diaminoheptane, 1,4-diaminobutane, 6-aminohexan-1-ol, 6-amino hexanoic acid, 2-aminoacetic acid, 2-amino-2-oxo-ethanoic acid, 4-aminobutanoic acid, ribose, arabinose, xylose, lyxose, galactose, mannose, 3-(2-hydroxyethyl)-2-oxazolidinone, hexane-2,5-dione, butane-2,3-dione, ethanedial, 2-hydroxybutanedial, 4-oxo-pentanoic acid, 1,4-butanediol, 1,6-hexanediol, 1,2,4-butanetriol, 1,2,6-hexanetriol, butanedioic acid, heptanedioic acid, oxoethanoic acid, 2,2-dihydroxyethanoic acid, 2,2'-oxybis(2-hydroxy)-ethanoic acid, 2-hydroxypropane-1,2,3 -tricarboxylic acid, 1,2,3,4-butanetetracarboxylic acid, 1,3-dioxolan-2-one, dimethyl carbonate, diethyl carbonate, diphenyl carbonate; 1,3-dioxan-2-one, 4-methyl-1,3-dioxolan-2-one, and mixtures thereof.

EXAMPLES

The following examples further describe and demonstrate the preferred embodiments within the scope of the present invention. The examples are given solely for the purpose of illustration, and are not to be construed as limitations of the present invention since many variations thereof are possible without departing from its scope.

Example Reducing Compositions

| | Example | | | | |
|---|---|---|---|---|---|
| Ingredient | 1 | 2 | 3 | 4 | 5 |
| Ammonium thioglycolate (48% in water) | 20 | — | 19 | — | — |
| Thioglycolic acid | — | — | — | — | 10 |
| Diammonium dithioglycolate (59% in water) | 10 | — | 8 | — | — |
| Ammonium thioglycolate (50% in water) | — | 21 | — | 20 | — |
| Diammonium dithiolactate (50% in water) | — | 9 | — | 10 | — |
| Ammonia (28%) | 1.9 | 1.8 | 1.9 | 1.8 | — |
| Polyquaternium-6 (40% in water) | — | 0.5 | 1.0 | 1.1 | — |
| Polyquaternium-7 (40 % in water) | 1.0 | 0.5 | — | — | — |
| Ceteareth-25 | — | 2.5 | 2.5 | — | — |
| Cetearyl alcohol | — | 5 | 6 | 4 | — |
| Cetyl alcohol | 5 | — | — | 2 | — |
| Ammonium bicarbonate | 1.3 | 1.2 | 1.3 | 1.1 | — |
| Beeswax | — | — | 1.0 | — | — |
| Preservatives [1] | 0.1 | 0.2 | 0.15 | 0.25 | — |
| Perfume | 0.2 | 0.1 | 0.07 | 0.1 | — |
| Deionised water | QSP | QSP | QSP | QSP | QSP |

KEY: See below.

Example Fixing Compositions

| | A | B | C | D | E | F | G | H |
|---|---|---|---|---|---|---|---|---|
| Arabinose | — | 10 | 10 | — | — | — | — | — |
| Ribose | 5 | — | 10 | — | — | — | — | — |
| Xylose | — | — | — | — | — | — | — | 1 |
| 2-hydroxypropane-1,2,3-tricarboxylic acid | — | — | — | 5 | — | — | — | — |
| 1,3-dioxolan-2-one | — | — | — | — | 5 | — | — | — |
| diethyl carbonate | — | — | — | 40 | — | — | — | — |
| 2,2-dihydroxyethanoic acid | — | — | — | — | — | 7.5 | — | — |
| Oxamic acid | — | — | — | — | — | — | — | 5 |
| Oxalic acid | — | — | — | — | — | — | 10 | — |
| 2,3-butanedione | — | — | — | — | — | — | 2 | — |
| 8-hydroxyquinoline | — | — | — | — | — | — | — | 0.01 |
| 8-quinolinol-1-oxide | — | — | — | — | — | — | — | 0.01 |
| Preservatives [1] | 1 | 1 | 1 | 1 | 1 | 1 | 1 | 1 |
| Fragrance | 2 | 2 | 2 | 2 | 2 | 2 | 2 | 2 |
| Viscosity-modifying agent [2] | 2 | 2 | 2 | 2 | 2 | 2 | 2 | 2 |
| Conditioning agent [3] | 1 | 1 | 1 | — | 1 | 1 | 1 | 1 |
| Deionised water buffered at pH 10 [4] | QSP | QSP | QSP | — | QSP | QSP | QSP | QSP |
| Deionised water buffered at pH 10 [4] and ethanol (1:1 ratio by volume) | — | — | — | QSP | — | — | — | — |

KEY: [1] = sodium benzoate;
[2] = Acusol 823 from Rohm and Haas; hydrophobically modified alkali soluble acrylic polymer emulsion (HASE);
[3] = epoxyaminosilane copolymer as described in EP2214633B1 (filing date 30th Oct. 2008) available from Momentive™ Performance Materials Inc., Columbus, Ohio, USA;
[4] = pH 10 buffer is a standard pH calibration buffer available from suppliers such as VWR, alternatively one can use water and modify the pH. Fixing composition E is in solid form; * = wt % after mixing in deionised water buffered at pH 10.

Example Methodology

Apply reducing composition onto hair and allow the hair to stand for 30 min. Rinse the hair with water and towel dry or blow dry the hair. Apply fixing composition onto hair and allow to stand for 30 min. Blow dry the hair. Flat-iron the hair at 121° C. to 232° C. (250° F. to 450° F.) to achieve the desired look. Heat and light-emitting hybrid straightening irons may be provided where a photocatalyst is used, for example, heat and light-emitting hybrid straightening irons at 250° F. (121° C.) and comprising an array of LEDs emitting UV light at 380 nm. Typically 5 to 10, e.g. 8 passes, of each lock of hair is carried out with the straightening irons.

PERFORMANCE DATA

Evaluation of Straightening Effect

FIG. 1 shows the straightening effect of hair treated with the method of the present invention versus comparative methods. Durability of the treatment is also tested. Experiment 1=reducing composition comprising 10% thioglycolic acid is applied onto hair, the hair is rinsed and dried, and then no fixing composition or oxidising agent is then used; experiment 2=reducing composition comprising 10% thioglycolic acid is applied onto hair, the hair is rinsed and dried, and then an oxidising agent (hydrogen peroxide at a level of 2 wt %) is then used; experiment 3=reducing composition comprising 10% thioglycolic acid is applied onto hair, the hair is rinsed and dried, and then a fixing composition (comprises 5% arabinose as crosslinking agent) is then used. In relation to the individual bars: A=immediately after treatment; B=after 1 wash; C=after 10 washes.

Evaluation of Hair Health

Figure 2:
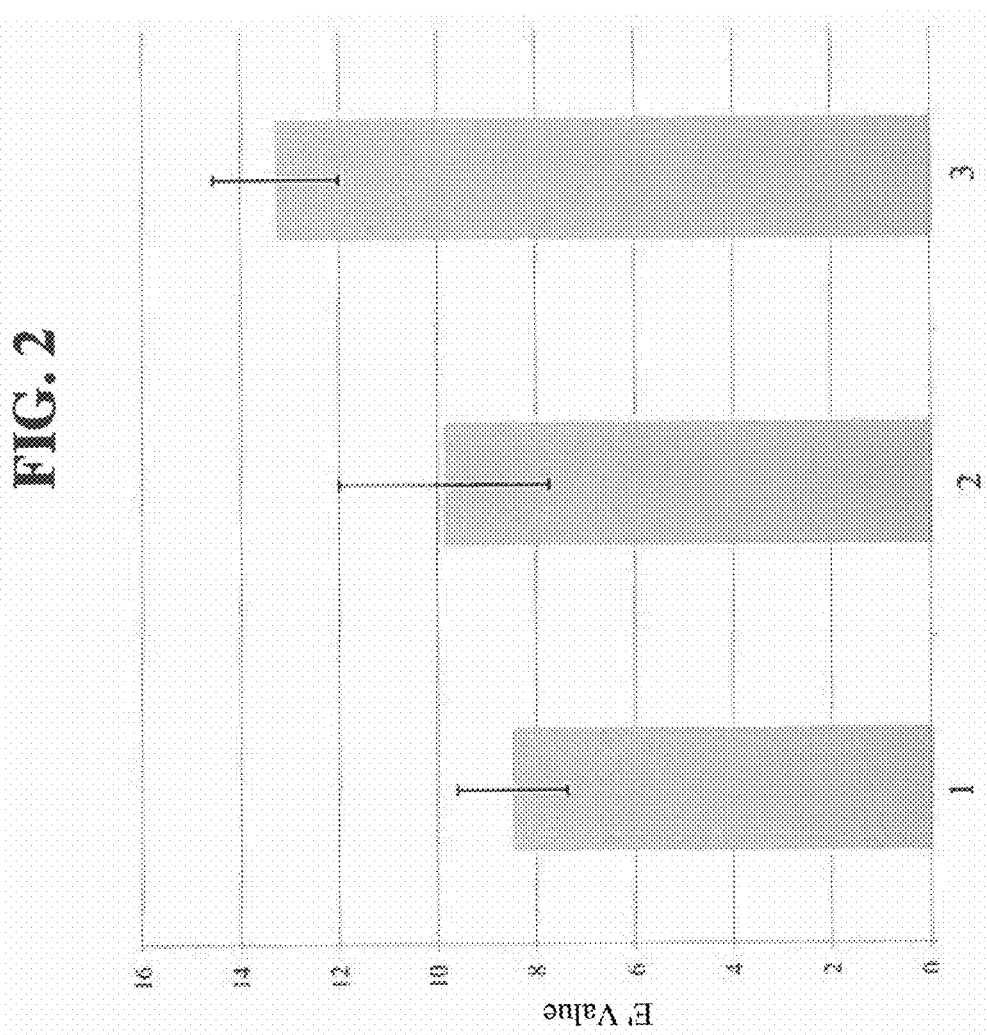
FIG. 2 shows a hair health experiment (presented as a bar chart) for hair treated with the method of the present invention versus comparative methods. 1=10% thioglycolic acid (TGA); 2=10% TGA+H$_2$O$_2$; 3=10% TGA+5% arabinose.

FIG. 2 shows a hair health experiment for hair treated with the method of the present invention versus comparative methods. In this experiment, the mechanical properties, namely the tensile strength of hair is tested. The hair is stretched within its elastic range, allowed to bounce back and then oscillate. The y axis measures the E' value, which is proportional to the structural integrity of the hair which is proportional to hair health. Single fibers are removed from the treated hair switches. Each hair fiber is clamped at its ends between the two parallel tensile plates. A frequency sweep (0.1 Hz-100 Hz) is conducted at 50% relative humidity to assess the mechanical properties of the fiber. A plot of E' and E" is determined versus frequency.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for straightening hair, wherein the method comprises:
    (a) applying a reducing composition to hair, wherein the reducing composition comprises from about 8% to about 12% of a reducing agent and from about 10% to about 20% urea as a hair swelling agent;
    (b) rinsing the hair and drying the hair;
    (c) forming a fixing composition on the hair by applying to the hair a composition which comprises about 12% to about 18% arabinose as the sole sugar fixing component, and a carrier comprising water or water-alcohol and subsequently applying from about 10 ppm to about 500 ppm of a photocatalyst to said arabinose composition;
    (d) drying the hair without rinsing it;
    (e) straightening the hair with a hair straightening appliance comprising metal or ceramic plates;
        wherein the arabinose composition is applied to the dried hair from step (b) at a level of 0.01 gram to 5 grams per gram of hair and remains on the hair for about 2-60 minutes prior to step (d);
    wherein the method does not use an oxidizing agent; and
    wherein (e) involves using an appliance whose plates are at a temperature of from about 50° C. to about 250° C. while exposing the hair to electromagnetic radiation having a wavelength of from 300 nm to 750 nm.

2. The method of claim 1, wherein the reducing agent is selected from the group consisting of: thioglycolate, thiolactate, and mixtures thereof.

* * * * *